United States Patent
Sarin et al.

(10) Patent No.: US 7,634,306 B2
(45) Date of Patent: Dec. 15, 2009

(54) NON-IMAGE, COMPUTER ASSISTED NAVIGATION SYSTEM FOR JOINT REPLACEMENT SURGERY WITH MODULAR IMPLANT SYSTEM

(75) Inventors: Vineet Kumar Sarin, Thousand Oaks, CA (US); Robert A. Bruce, Ventura, CA (US); William Ralph Pratt, Newbury Park, CA (US); Clyde Ronald Pratt, Somis, CA (US)

(73) Assignee: Kinamed, Inc., Camarillo, CA (US)

( * ) Notice: Subject to any disclaimer, the term of this patent is extended or adjusted under 35 U.S.C. 154(b) by 780 days.

(21) Appl. No.: 10/703,980

(22) Filed: Nov. 6, 2003

(65) Prior Publication Data

US 2004/0097952 A1  May 20, 2004

Related U.S. Application Data

(63) Continuation-in-part of application No. 10/075,796, filed on Feb. 13, 2002, now Pat. No. 6,711,431.

(51) Int. Cl.
*A61B 5/05* (2006.01)
(52) U.S. Cl. .................. 600/426; 600/429; 606/130
(58) Field of Classification Search .............. 623/22.11; 600/424; 702/150
See application file for complete search history.

(56) References Cited

U.S. PATENT DOCUMENTS

| | | | |
|---|---|---|---|
| 4,475,549 A * | 10/1984 | Oh | 606/91 |
| 5,249,581 A * | 10/1993 | Horbal et al. | 600/407 |
| 5,807,252 A | 9/1998 | Hassfeld et al. | |
| 5,828,770 A | 10/1998 | Leis et al. | |
| 5,880,976 A * | 3/1999 | DiGioia, III et al. | 703/7 |
| 6,061,644 A | 5/2000 | Leis | |
| 6,204,411 B1 | 3/2001 | Axon et al. | |
| 6,381,783 B2 | 5/2002 | Reinhardt | |
| 6,711,431 B2 | 3/2004 | Sarin et al. | |
| 2002/0111643 A1 | 8/2002 | Herrmann | |
| 2003/0056385 A1 | 3/2003 | Leitner | |
| 2004/0153191 A1 | 8/2004 | Grimm | |
| 2004/0167654 A1 | 8/2004 | Grimm | |

* cited by examiner

*Primary Examiner*—Corrine M McDermott
*Assistant Examiner*—Christopher D Prone
(74) *Attorney, Agent, or Firm*—Koppel, Patrick, Heybl & Dawson

(57) ABSTRACT

The invention includes a method and system for intra-operative navigation of a joint replacement operation, without recourse to pre-operative imagery of pre-operative computerized simulations. Trackable markers and a locating system are employed to track first and second bones. A computer receives positional information regarding the trackable markers and calculates (predicts) at least one suggested combination of components of a modular implant system to produce a desired post-operative skeletal relationship.

29 Claims, 9 Drawing Sheets

IMPACTOR POSITION

SHELL POSITION

LINER POSITION

HEAD CENTER CHANGE

LEG LENGTH CHANGE

HEAD OFFSET CHANGE

NOTE: RIGHT PEDAL SEND SUMMARY TO PRINTER, ALONG WITH PATIENT DATA. SAVE ALL DATA TO FILE SPECIFIC TO THIS RUN OF SOFTWARE. CHANGE SECURITY FLAG SO THAT SAME CD CAN NOT BE USED TO START PROGRAM AGAIN.

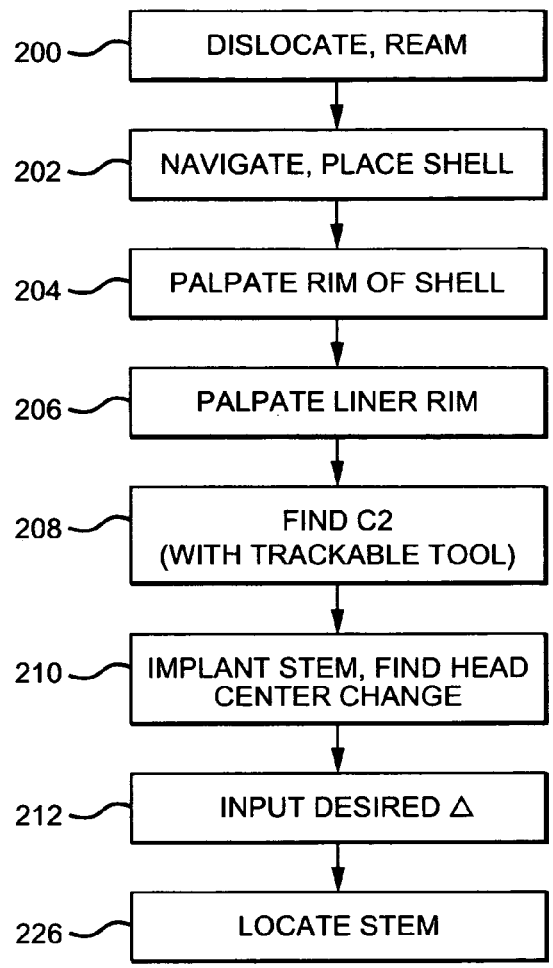
*FIG. 12a*
*FIG. 12*
| *FIG. 12a* |
| *FIG. 12b* |
| *FIG. 12c* |
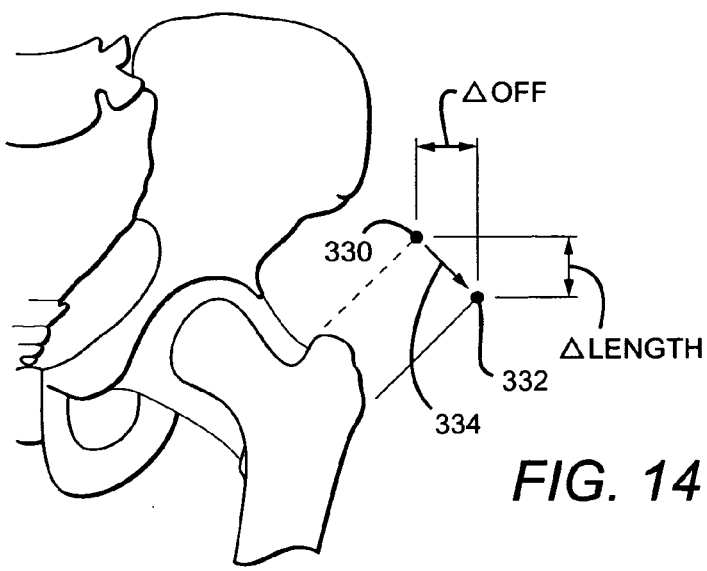
*FIG. 14*

NON-IMAGE, COMPUTER ASSISTED NAVIGATION SYSTEM FOR JOINT REPLACEMENT SURGERY WITH MODULAR IMPLANT SYSTEM

This application is a continuation-in-part of U.S. patent application Ser. No. 10/075,796 filed Feb. 13, 2002, now U.S. Pat. No. 6,711,431 and claims priority of that application as to matter disclosed therein. This application further claims priority of application Ser. No. 10/637,304 filed Aug. 8, 2003 (with priority of provisional application 60/402,179 filed Aug. 9, 2002) as to matter disclosed therein.

BACKGROUND OF THE INVENTION

1. Field of the Invention

This invention relates to computer assisted surgery generally and more specifically to computer assisted total hip replacement (THR) or hip arthroplasty operations.

2. Description of the Related Art

Total hip replacement or arthroplasty operations have become increasingly common in the United States, with more than 300,000 such operations occurring annually. Many of the procedures will eventually require revision, due to one of any number of problems. Problems can arise with the implant, which can wear, degrade or even fracture. In other cases, dislocation of the replaced hip can occur, causing extreme pain (not to mention inconvenience and expense). The incidence of dislocation has remained at approximately 2-6 percent, in spite of improvements to technique and materials.

It is known that the incidence of post-surgical dislocation is related to the orientation and fit of the hip replacement components, particularly to the angular orientation of the acetabular shell component in relation to the bony anatomy. See Lewinnek et al., "Dislocation after total hip-replacement Arthroplasties," *Journal of Bone and Joint Surgery*, Vol. 60A, No. 2, PP. 217-220 (1978). The head and neck geometry of the femoral implant is also thought to be a factor.

In spite of the published research, the typical surgeon has not adopted any sophisticated method of navigating hip replacement surgery, in spite of the availability of several techniques. The most prevalent method is to rely on an acetabular insertion tool with a handle placed at an angle predetermined so that if the handle is maintained at a predetermined orientation, the acetabular shell will be at a desired angle. This method fails to consider the considerable movement and variation in the patient's pelvic position during surgery; at worst it aligns the shell with the operating-room table (not necessarily the pelvis). More technological methods have been developed, including the sophisticated method described in U.S. Pat. No. 6,205,411 (and related applications) to DiGioia et al. (2001). The method of DiGioia is an advance over the prior methods (which he summarizes authoritatively in his "Background" section).

DiGioia's method begins with extensive preoperative imaging, including relatively expensive CT scanning. The pre-operative imagery is then input into a digital computer model, which performs extensive, three-dimensional modeling including range of motion simulations of the patient's anatomy in relation to a specific computer model of a particular implant,. Next, in an intra-operative phase, the pre-operative models are registered using intra-operative optical tracking data: a very large number of points are sampled on the pelvis and femur, and the computer fits the data to the pre-operative model. Finally, the implant is positioned to align as closely as possible with the optimized computer model.

The method of DiGioia et al. is complex and requires sophisticated digital and radiological techniques. A need still exists for a simpler method of surgical navigation which will facilitate proper hip geometry with a minimum of pre-operative imagery and expense. It is frequently found that physicians are loath to adopt any methods, and particularly any computerized methods, which are unduly complex, expensive or time consuming. In this they may be forgiven, in light of the increasing economic constraints which burden the modern practice of medicine.

Thus, a need persists for an intra-operative computer assisted hip navigation system which is easily learned, rapidly executed, economically practical, and independent from expensive or exotic pre-operative radiological imagery.

SUMMARY OF THE INVENTION

In view of the above problems, the present invention includes a method and system for intra-operative navigation of a joint replacement operation, without recourse to pre-operative imagery or pre-operative computerized simulations.

The system of the invention includes a modular implant system, having a plurality of components, adapted for assembly according to a plurality of assembly options to allow adjustment of the implant geometry. In one embodiment, at least one of the components has one or more index features. During joint replacement surgery (for example, hip replacement surgery) two trackable markers are fixed: one to a first bone (for example, the pelvis) and the other to a second bone (for example, the femur). Optionally, a trackable tool is adapted to be positioned in contact with an index feature. A locating system tracks the two trackable markers (and optionally the trackable tool), and provides positional information which is output to a computer. The computer receives the positional information and digitally models a relationship of the modular joint implant system to the first and second bones of the patient. The computer then accesses a database of component parameters and calculates (predicts) at least one suggested combination of components to produce a predetermined, desired post-operative skeletal relationship. Said post-operative skeletal relationship preferably includes both dimensional and directional relationships, such as both bone displacements and angular relationships among bones and/or modular implant component structures.

In accordance with the invention the predicted post operative skeletal relationships include: displacement between the first and second bones, direction of the displacement, and angular relationships among the bones and/or implant components. For example, in a hip replacement surgery the method aids in producing desired relationships including one or more of: changes in leg length, medial/lateral leg offset, hip neck angle, and stem anteversion.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 12a is a flow diagram showing detailed steps suitable for executing the navigation step of FIG. 2;

FIG. 14 is a frontal view of a hip joint and pelvis, illustrating the geometry and defining a relative offset and leg length, as determined in the method of the invention;

DETAILED DESCRIPTION OF THE INVENTION

Overview

Throughout the description of the invention, reference will frequently be made to "tracking" or "trackable markers." This terminology is intended to denote any of several available methods of tracking objects in three dimensions without unwieldy mechanical frameworks or measuring devices. In the most preferred embodiment of the invention, optical tracking is employed, using optically trackable markers such as those available from Traxtal in Toronto, Canada. Similarly, in the description we will refer to a "locating system." In a preferred embodiment of the invention, the locating system will be an optical, computer aided locating system such as the "Polaris" system available from Northern Digital Inc. in Waterloo, Ontario, Canada. However, it should be understood that other methods of tracking, locating systems, and trackable markers could be employed without departing from the invention. For example, magnetic, electromagnetic, ultrasonic, sonic, infrared, or microwave tracking could be substituted for optical tracking and optically trackable markers. Combinations of these methods could be employed; for example, a hybrid optical/magnetic tracking system. On the other hand, it is not intended that "tracking" include position acquisition by conventional mechanical measurement, mechanical stereotactic frameworks or electromechanical stereotactic frameworks. Such methods are inconvenient and tend to interfere with free access to the surgical field.

As used in this specification and in the claims which follow, the word "optical" should be understood to include techniques involving any light wavelengths, including infrared, visible or even ultraviolet wavelengths.

Figure 1:
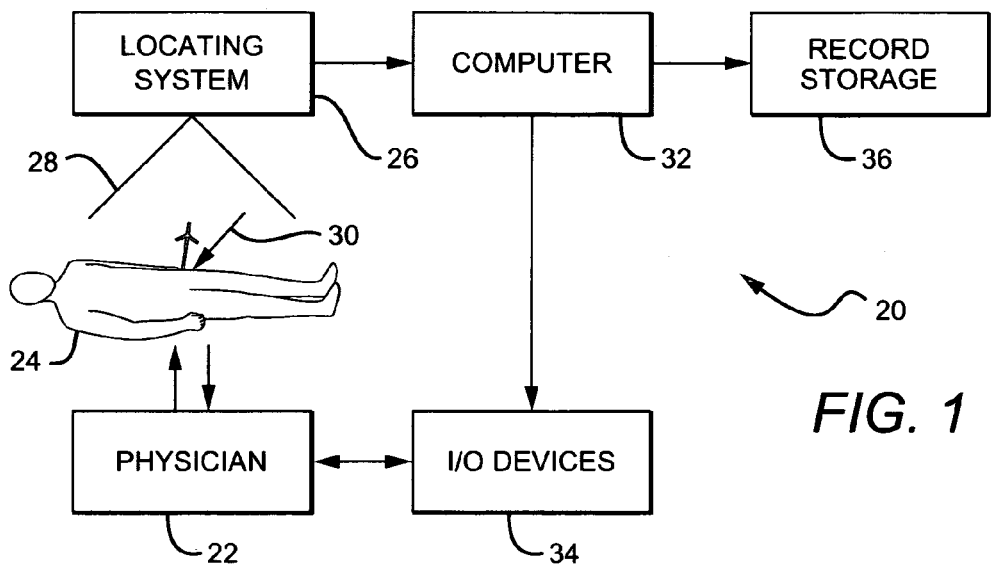
FIG. 1 is a system-level block diagram of the apparatus of the invention in a typical surgical environment.

FIG. 1 shows a system-level block diagram of the system or apparatus 20 of the invention in a typical operating room environment. A physician or other professional 22 performs a joint replacement surgery (for example, total hip replacement) on a patient 24. An optical or equivalent locator or locating system 26 is disposed near the patient, so that the operating field is encompassed substantially within the field of view 28 of the locator 26. A suitable optical locator is available commercially, for example the "Polaris" available from Northern Digital Inc., in Waterloo, Ontario, Canada. Trackers or markers 30 (preferably optical) are used during the operation, as more fully described below. The markers 30 allow the locator 26 to acquire the positions and orientations of tools and anatomical reference points, as described below.

The markers 30 could optionally be either active (for example, light emitting diodes) or passive (reflectors, for example). Similarly, the markers could be either wired or wireless without departing from the invention, which does not depend upon use of any particular type of marker.

The locating system 26 is interfaced with and outputs tracking data to a digital computer 32, which interprets the optical tracking data as it is received. Using well known geometric relationships, the computer is programmed to deduce from the field of view the actual positions and orientations of the markers, and, by extension, the positions and orientations of the instruments and/or anatomical features that are in known relationship to the markers. For example, suitable optical markers utilizing multiple reflective spheres are available from Traxtal, Inc. in Toronto, Ontario, Canada. Markers with active light emitting devices such as LEDs are also available and could equivalently be used. Note that typical markers include two or more (non-collinear) components; this allows the locator and computer to determine not only the positions but the orientation (rotation) of such a marker in space. This capability is exploited in the methods described below.

A calibration file can be loaded onto the host computer that describes the tracker and the relationships between the markers on the tracker. Such files and techniques for using them are defined and are available from Traxtal and Northern Digital Inc., mentioned above.

Preferably, the computer 32 is also programmed with a user-friendly interface (software) which facilitates the execution of the method of the invention (described below in connection with FIG. 2). The physician or other personnel can view output (for example on a video monitor) and input instructions to the computer 32 via I/O devices 34, which suitably could include a monitor, keyboard, printer, foot pedals, and other input/output devices such as conventional "mouse" or similar pointing devices.

Preferably, the system also includes a record storage device 36 such as a computer readable storage (magnetic, optical or other media), and/or simply a printer which prints out a summary of the operation and patient data for future reference or medical archiving.

General Method

For convenience, the procedure of the invention will be discussed and illustrated in the context of a hip replacement surgery. However, the method is not limited to hip replacement surgery but rather could be employed in any joint replacement procedure in which a joint between a first bone and a second bone is to be replaced. For example, the method could be employed in connection with knee, ankle, hip, shoulder, elbow, wrist, spine, finger, or vertebral disc surgery; or any other surgery where there is a need to insert an implant in an aligned position or relationship with the anatomy. The method does offer particular advantage in connection with hip replacement surgery; and accordingly, the discussion which follows will describe the particular embodiment of the invention for hip replacement surgery.

Figure 2:
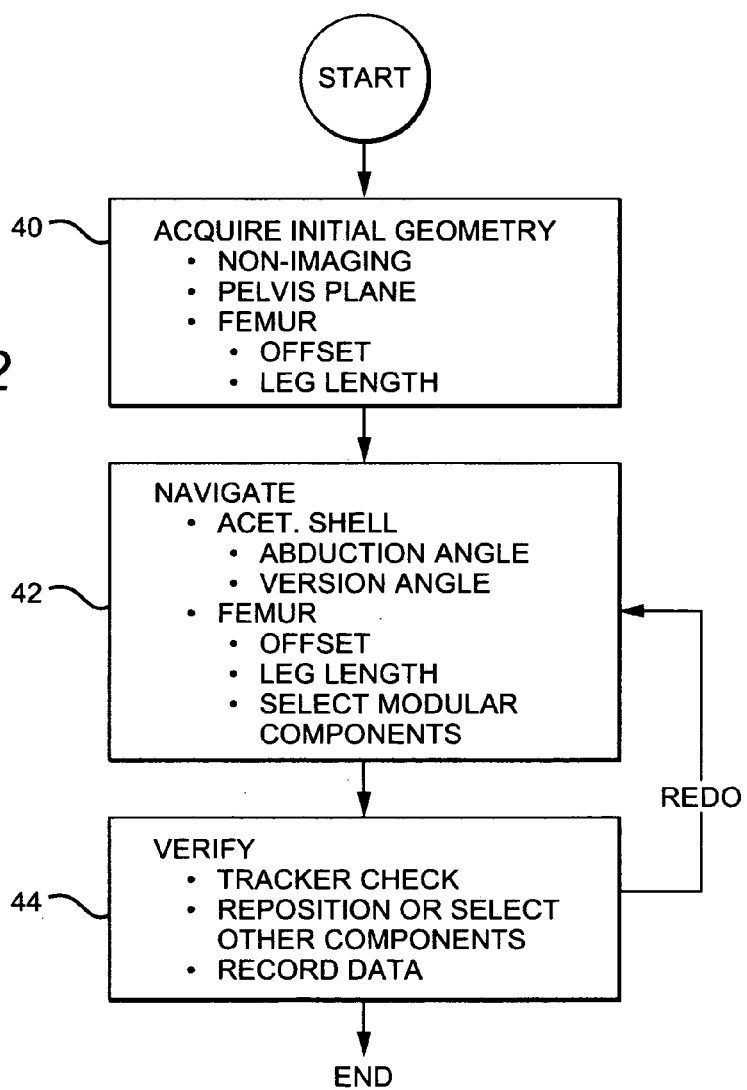
FIG. 2 is a high-level flow diagram of the method of the invention.

FIG. 2 is a top-level flow diagram of the method of the invention, showing the steps of the method at a high level of abstraction. Specific steps are elaborated and explicated in connection with later figures, along which particular surgical apparatus suitable for practicing the method.

In broad terms, the method includes three major steps, all performed intra-operatively: Acquisition of patient geometry (40), computer aided navigation of surgery (42), and computer aided verification (44) of implant geometry.

Patient geometry is acquired (in step 40) by attaching and optically tracking several optically trackable markers, described below in connection with FIGS. 3-5. Note that the acquisition of patient geometry according to this method does not utilize any radiographic or other imaging.

After acquiring the initial or "native" geometry of the patient's pelvic-femoral system, in step 42 the method uses continuous or near-continuous, real-time optical tracking of the pelvis and femur as well as surgical tools, including an optically trackable insertion or equivalent tool for positioning and fixing an acetabular shell implant. Computer acquired and calculated information is displayed to the surgeon in real time to facilitate placement of the acetabular shell implant within a desired angular range of anteversion and abduction (or a desired range of anterior/posterior angulation or "flexion"). The femur is also tracked and computer graphic display allows the surgeon to achieve a desired amount of femoral offset and a desired leg length (typically very nearly matching the native length and offset on the opposite side of the body).

In accordance with the invention, step 42 also includes a method of using the optical locating system 26 and computer 32 to facilitate choice or adjustment of at least one component of a modular hip implant system. "Modular" implant systems are commercially available for hip and other orthopedic implants. Such implant systems have a plurality of components which can be assembled in combination to produce a complete implant. Each component of the system is made available in more than one size, model, or geometry, for selection by a surgeon. Thus, by choice of (interchangeable) modules, the overall geometry of the assembled system can be greatly varied. This gives the surgeon an ability to somewhat customize the implant system for an individual patient. For example, modular hip implant systems are available having separate stem, neck, and head components, each available in different sizes or geometries. In some systems, the modules may also be adjusted during assembly, providing additional freedom to customize.

The use of the optical tracking system and computer in accordance with the invention allows more accurate and more expeditious choice of modules or adjustment of a modular hip implant. A more detailed explanation of a method of using the invention with a modular hip implant system is given below, in connection with FIGS. 12-12c. In many cases this procedure can diminish the number of trial reductions and dislocations required, thus reducing time in the operating room and overall cost of the procedure. In addition, the procedure described can enhance accuracy and control of the implant geometry, better match the modular implant to the desired geometry and reduce the incidence of failures, dislocations, or other problems requiring revision.

Finally, in step 44 the orientation and position of pelvic and femoral tracking markers are preferably verified by optical tracking and computer calculation, by a method of redundant checking ("tracker check") . This step reveals any inconsistencies, such as might occur due to slippage, loosening, or bending of instruments, or other errors. If any significant discrepancy is revealed during verification, the surgeon has the option to repeat some or all of the surgical procedure before terminating the procedure.

Preferably, the verification step 44 also includes making and storing permanent records of the procedure, including patient and implant geometry, for archiving or medical reference. The record can be in machine readable, and/or human readable form. For example, a printout is preferably generated which can be entered into a traditional medical filing system, together with a machine-readable record of the operation, for example on CD-R, or magnetic media such as a "floppy" or hard disk.

Optically Trackable Markers and Tools:

The more detailed procedural explanation given below in FIGS. 8 through 13 makes frequent reference to certain optically trackable markers and tools which are specifically adapted for the invention. Visualization of the procedure thus will be greatly facilitated by first considering typical trackable markers and tools.

Figure 3:
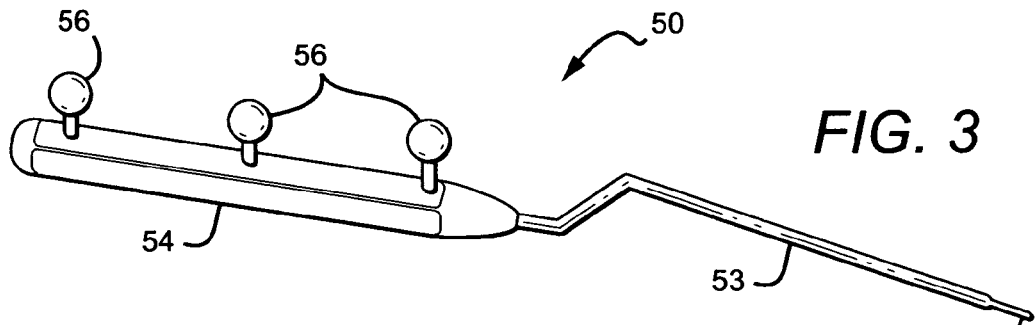
FIG. 3 is a perspective view of an optically trackable manual probe suitable for use to input positional information in the method of the invention.

A typical optically trackable manual probe 50 is shown in FIG. 3. This probe includes a pointable tip 52 at the front end of an elongated stem 53 of known length and shape. The rearward end of the stem 53 is fixed to a rigid body 54 of known dimensions and geometry, suitably shaped for hand-gripping. Mounted to the body 54 is an optical tracking target 56 having at least two, and preferably three or more optical tracking references. Both active and passive references, targets, and probes are available commercially, for example from Traxtal, Inc. in Toronto, Ontario, Canada.

It is known that an optical tracking target such as 56, with known dimensions and geometry, can be optically tracked for example by an optical locating system available from Northern Digital, Inc. (referenced previously). Since the dimensions and shape of the stem 53 and body 54 are known, tracking of the position and orientation of target 56 allows ready calculation of the position of the tip 52 by well known geometric relationships. Thus, to enter a spatial location (such as an anatomical landmark) into to computer 32, a physician can touch the tip 52 to the location while simultaneously cueing the computer to input the instant position. A foot switch is a typical and convenient method of cueing the input.

Figure 4:
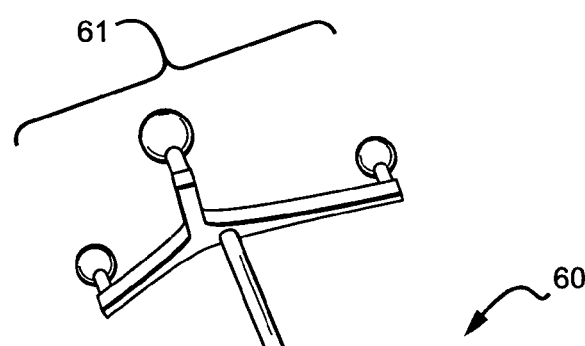
FIG. 4 is a perspective view of another optically trackable position marker suitable for fixation to the pelvis for tracking the position and orientation of the pelvis.

FIG. 4 shows a similar optically trackable pelvic marker shown generally at 60, which includes a trackable marker 61 adapted for fixation on a bone screw 62, and suitable for intra-surgical fixation to any convenient surface of the pelvic bone. Note that a quick release device 64 is preferably provided between the target 61 and the bone screw 62. The quick release device 64 allows the trackable marker 61 to be quickly attached or detached as required during surgery. Detachment of the marker 61 is convenient for the surgeon, lest he find his movements encumbered by its presence. The quick-release device should be designed to provide well defined, stable, and reproducible positioning of the marker 61 with respect to the bone screw 62 (and, by implication, with respect to the bone).

Figure 5:
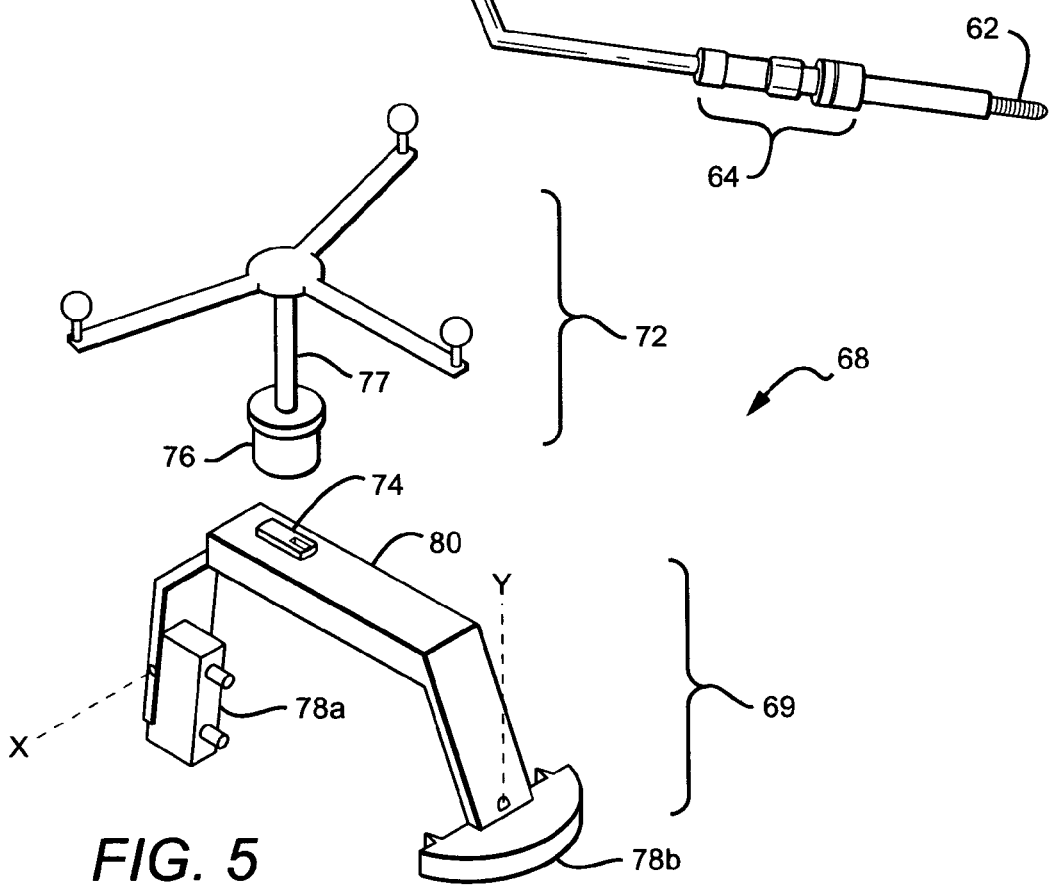
FIG. 5 is a perspective view of yet another optically trackable marker adapted for fixation to the femur to track position and orientation of the femur.

FIG. 5 shows generally at 68 a femoral tracking marker capable of clamping attachment to a first bone of a patient (for example, on the femur near the greater trochanter). It is extremely preferable that this device be fixable to the first bone (femur) in a firm and fully engaged position which does not allow slippage or rotation, but without the use of bone screws, pins or any other bone penetrating devices. Specifically, the marker 68 is attachable by clamping without fully penetrating the outer cortical (hard) shell of the bone. It is permissible, in accordance with the invention, to use aggressively textured surfaces, which could include spikes or cleats which superficially penetrate but do not significantly compromise the outer cortical shell.

As shown in FIG. 5, one embodiment of the trackable femur marker 68 comprises: a removable bone clamp 69; a trackable optical marker assembly 72; and a releasable coupling 74, integrated with or fixed to the bone clamp and arranged to mate with a compatible coupling 76 on the trackable marker assembly 72. Preferably, the coupling permits releasable connection between the target and the bone clamp in such a way that a reliable, repeatable spatial relationship is maintained between the bone and the trackable target whenever the coupling is in mated position, notwithstanding any disconnect/reconnect cycles of the coupling (provided that the bone clamp has not been relocated vis-a-vis the clamped bone).

The trackable marker assembly 72 is preferably mounted on an elongated stem 77. The stem in turn is coupled via the releasable coupling 74 and 76 to the bone clamp 69. The bone clamp includes two opposable, pivotable jaws 78a and 78b: a first jaw 78a pivotable about a first axis (arbitrarily, x) and a second jaw 78b pivotable about a second axis (y). As the figure shows, the first and second axes are constrained to be substantially non-parallel, and in fact the axes are preferably constrained to be substantially perpendicular to one another. The two jaws are pivotably connected at opposite ends of a bracket 80, which is preferably adjustable by some mechanism such as a tightening screw. The clamp can be attached to a bone by first positioning the jaws in opposition with the greater trochanter disposed between them. The bracket 80 is then tightened by shortening its length with the adjustment mechanism, thereby urging the opposed first and second jaws toward each other to clamp or pincer the femur near the greater trochanter.

Figure 6:
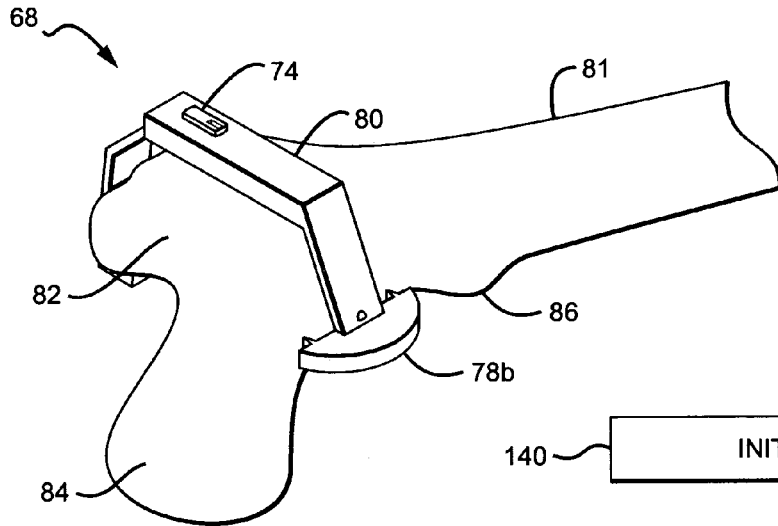
FIG. 6 is a plan view of a clamp of FIG. 5, in operative position clamped to a femur without penetrating devices or screws.

FIG. 6 shows the bone clamp portion of the femoral tracking marker assembly of FIG. 5 in position: fixed to a femur 81 by clamping about the greater trochanter 82. This figure shows a suitable manner of mounting the femoral fixing device on a human femur. Specifically, the first jaw 78a is arranged to engage the anterior aspect of the greater trochanter; the second jaw 78b is arranged opposite, with the bone interposed between the jaws. The femoral head 84 and lesser trochanter 86 are also shown as landmarks.

The clamp is shown with the marker 72 and stem 77 removed (by disconnecting the releasable coupling). One member of the releasable coupling 74 can be seen at the top of the bracket; the complementary member 76 is associated with the stem and marker and thus is not visible in this figure.

The releasable coupling facilitates surgery as follows. During surgery, as described above, the femoral tracking marker is initially clamped to a patient's femur with a trackable target initially coupled to the clamp by the releasable coupling. The optical tracker tracks the femoral tracking marker during initial geometry acquisition as described below ("Acquisition of Initial Patient Geometry"). Thus, an initial relationship between the femoral tracking marker and the pelvis is captured and recorded or stored, corresponding to an initial reference position for offset and leg length.

Once an initial geometry has been captured, the releasable coupling feature allows a physician to remove the optical marker portion of the femoral tracking marker 68, including the stem 77, to gain more convenient surgical access to the hip and femur. The bone clamp 69 portion of the femoral tracking marker remains securely fastened to the femur. The optical target then can subsequently be reattached to the bone clamp 69 via the coupling 74 and 76, and the previous relationship between the target and the bone will be accurately and reliably reestablished. Reliable optical tracking of the femur can then resume (for example during the navigation steps as described below).

The femoral tracking device according to the invention could alternatively be described as an optically trackable target, capable of fixation to a bone, including: an adjustable bracket having first and second ends and an adjustment mechanism connected to adjust the displacement between the first and second ends; at least two jaws, one connected to each end of the adjustable bracket; a releasable coupling integrated with the bracket; and an optically trackable member having a compatible coupling which is capable of mating with said releasable coupling in a predictable and repeatable position and orientation. The optically trackable member may optionally be displaced from the coupling and clamp by a substantially rigid stem or other member, which need not be linear in form.

The femoral tracking marker 68 of the invention is extremely advantageous and is preferred over prior devices such as bone screw tracking devices (such as that described in U.S. Pat. No. 5,807,252 to Hassfeld et al.). Such bone screw devices are commonly used in knee replacement surgery. The upper femur, however, is less amenable to bone screw attachment. Because of the mechanics of the hip and upper femur, the upper femur experiences very large stress and shearing forces, both in its natural state and after implantation of an artificial hip prosthesis. In extreme cases this stress can actually cause the prosthetic stem to fracture the upper femur. Thus, it is desirable to avoid placement of any penetrating device such as a bone screw into the upper femur, as the penetration could compromise the structural integrity of the bone tissue.

Structural integrity is not the only reason for avoiding use of bone screws in the femur during hip replacement surgery: during preparation of the femur to receive a stem component, the femur canal is cleared of bone using drills and broaches, to make a cavity for the implant stem. Presence of a deeply penetrating bone screw would interfere with drilling and broaching operations, and in some cases would actually mechanically interfere with proper insertion of the stem component. The femoral tracking device of the invention thus permits convenient and quick attachment without fully penetrating the outer cortical (hard) shell of the femur, and without interfering with drilling, broaching, and stem insertion.

Alternatively, another femoral tracking device including a ligature, fixable to the femur and/or the greater trochanter, could be used to attach the tracking marker to the femur.

Figures 7, 16:
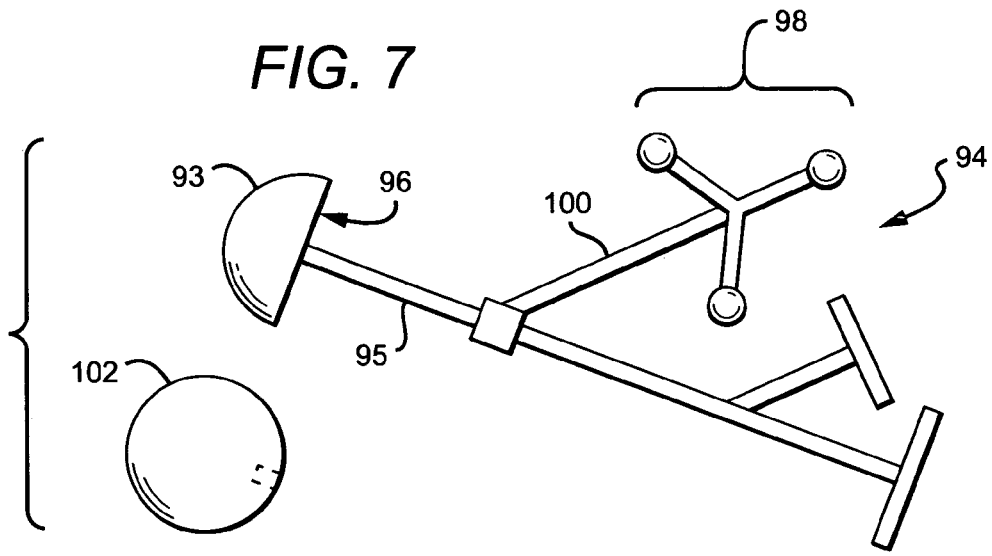
FIG. 7 is a perspective view of an acetabular component placement and measurement tool ("impactor") equipped with a tracking marker in accordance with the invention.
FIG. 16 is a typical printout/record produced by the method of the invention for archiving and/or retention in the patient's medical records.

One further trackable tool is useful. FIG. 7 shows an acetabular shell component 93 mounted on the insertion placement tool 94. Typically the shell component 93 is essentially a sliced spherical shell, which may be hemispherical or describe more or less than half of a sphere. The insertion tool 94 preferably has a shaft 95 which is fixable to the shell 93, for example by a pressed fit or threaded mating device. Once fixed, the shaft is held at a known orientation with respect to the shell. It is particularly convenient if the shaft 95 is fixed normal to the plane of the lip 96, as shown in the figure. An optically trackable marker 98 is mounted to the insertion shaft 95, but offset by a secondary shaft 100 (which may optionally include a quick release device). The marker 98 is held in fixed angular relation to the insertion shaft 95, so that by locating the orientation of marker 98, the angle of the shaft 95 is easily also determined. This tool is employed during the "navigation" and modular component selection steps of the method (described below, in connection with FIGS. 12*a*-12*c*). The preceding discussion of the preferred optical tracking markers should be borne in mind while considering the following detailed procedural descriptions of the preferred method of the invention.

FIG. 7 also shows a removable head 102 adapted for fixation on the insertion shaft 95. The removable head 102 is partial sphere with known diameter and center in fixed, predetermined relationship to the shaft coupling system (for example, a "morse taper" of the shaft which mates with a compatible female taper in the head). This removable head tool can be used to find the modified head center of the prosthetic acetabular cup (and liner) as described below in connection with FIGS. 12*a*-12*c*.

Figure 8:
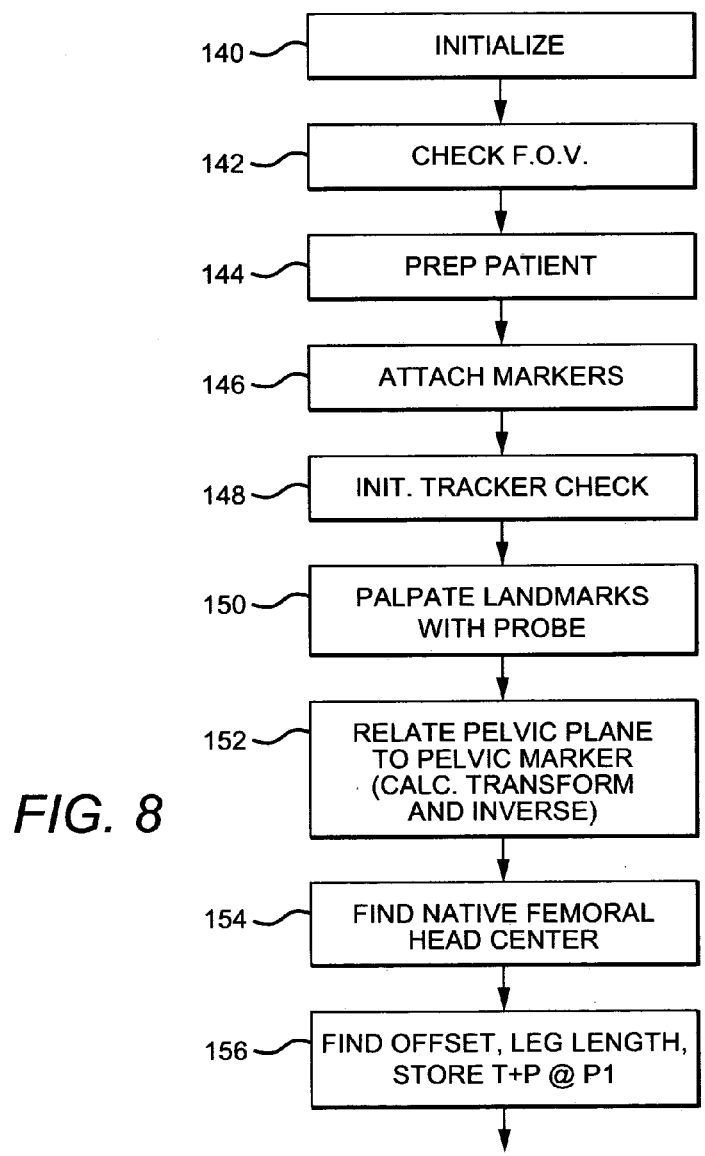
FIG. 8 is a flow diagram of detailed steps suitable for executing the acquisition step of FIG. 2.

Acquisition of Initial Patent Geometry:

FIG. 8 shows in greater detail preferred steps which are included in the acquisition step (40 in FIG. 2). Preliminary steps 140-144 are conventional. In step 140, the system is initialized: a welcome screen appears and the physician or other professional enters relevant patient and physician information. Next (step 142) the physician checks the field of view with an optically trackable pointer such as that described above in connection with FIG. 3. The surgical field should be arranged to lie substantially within the field of view 28 of the optical tracker 26 (in FIG. 1) yet close enough to the optical tracker to allow a high degree of tracking accuracy. Next the patient is prepared for surgery in a conventional manner and introduced into the field of view (step 144).

Note that no pre-operative computer modeling or high-resolution radiological imaging (such as a CAT scan) are included in the method of the invention (although a physician typically will have consulted previous X-ray images before surgery).

Next, in step 146, the physician attaches at least one pelvic marker 60 and at least one femoral tracking device 68 (discussed above in connection with FIGS. 4 and 5). The pelvic tracking marker 60 is suitably attached by inserting a bone screw or other fixing device into a portion of the pelvic bone. In contrast, according to the invention the femoral tracking marker 68 is attached without penetrating bone screws, as described previously (or as described below in connection with FIG. 15). By avoiding insertion of bone screws into the femur, the invention prevents injury or mechanical compromise of the highly stressed upper femur, thereby lessening the likelihood of post-operative complications due to femoral fracture. The femoral tracking marker 68 also does not impede access to the femoral stem and femoral canal.

After attaching the tracking markers, in optional step 148*a* a redundant accuracy check is initialized ("Tracker check"). Preferably, a redundant reference mark is placed on the pelvis at some position other than that of the fixed pelvic tracking marker. Cauterization is a suitable and convenient method of marking the pelvis, but other methods could also be used. The physician then touches the redundant reference mark with an optically trackable probe (50 in FIG. 3) while cueing the computer (for example by foot switch) to input the tracker's position. The computer then calculates the position of the redundant reference mark in relation to the pelvic tracking marker (in other words, in a pelvic tracking marker reference frame or "PTMRF"). The vector thus defined is stored for future reference (during navigation steps, described below).

Next, in pelvic definition step 150, the physician uses the optically trackable manual probe 50 to palpate at least three, and preferably four, easily located anatomical landmarks on the pelvis. This is accomplished, for each landmark, by activating a foot pedal or other switch while simultaneously positioning the probe in percutaneous contact overlying a prominent anatomical landmark. When thus cued, the computer 32 receives positional information regarding the probe from the optical tracking system 26 and calculates from this information a position for the corresponding landmark in a reference frame attached to the pelvic marker 60.

The reference landmarks in the pelvic definition step 148 are suitably chosen from: the ipsilateral anterior superior iliac spine (ipsilateral "ASIS"), the contralateral anterior superior iliac spine (contralateral "ASIS"), the ipsilateral pubic tubercle, the contralateral pubic tubercles (or the midpoint of the pubis between the tubercles. Basic geometry dictates that at least three points are required to define a plane. Three points may suitably be used. However, more than three of the above mentioned reference landmarks may be input into the computer system to better define the anterior pelvic plane. One suitable method is to define an imaginary point at the midpoint of the line segment between the two pubic tubercles. This midpoint is then used, together with the two ASIS, to define the anterior pelvic plane. Suitably, the computer can choose a plane by a least squares minimum error fit to the four points, if any asymmetry exists. A Pelvic Coordinate frame of reference is also defined in this step, suitably with origin at the midpoint between the ASIS. A suitable coordinate frame is more fully described below in connection with FIGS. 9 and 10.

Note that the pelvic reference plane ("anterior pelvic plane") is an imaginary plane defined by 3 points; no effort is made to curve fit to a complete, non-planar model of the pelvic bone. Indeed, no such model is assumed to be available, as no pre-operative CT or MRI scan is required by the method.

Next, in step 152, the computer relates the anterior pelvic plane (calculated from step 150) to the reference frame of the pelvic tracking marker. That is to say that the pelvic tracking marker, firmly attached to the pelvic bone at some hitherto unknown orientation, defines a pelvic tracking marker reference frame (PTMRF, an orientation and position of the marker). The pelvic coordinate system that was calculated in step 148 is related to the PTMRF by a rotation and translation, and this relationship is calculated and stored. Differently stated: The pelvic reference frame found by palpating landmarks defines a first coordinate system; the position and orientation of the fixed pelvic tracking marker defines a second coordinate system, related to the first by an affine transformation. The affine transformation $T_{pf}$ (and preferably the inverse transformation $T_{pf}^{-1}$) are calculated by well known means and stored. In a typical mathematical model, for three dimensions the coordinates in each reference frame can be considered 3-vectors; the transformation can be represented by a 3×3 matrix, as is well known.

Next, (step 154) the physician (in coordination with the program execution of computer 32) pivots the femur, typically in arcs or circles consistent with its natural arcs of movement. The movements of the femoral tracking marker are tracked by the optical locating system 26 and interpreted by the computer 32 to calculate the natural or "native" femoral head center (referred to as "C1"). This is suitably accomplished by assuming that the motion of a point on the femur is constrained to lie on a partial spherical surface with its center at the native head center. A least squares surface fitting. algorithm is suitably used to calculate the center of the sphere (C1). Alternate methods of finding the native center are also possible: for example, the physician could pivot a well-fit shell (or sphere) in the native acetabulum while tracking the axis of the shell (or sphere). (Note that if this alternate method is used, it must necessarily be performed after dislocation; this implies that a femoral length and offset reference position must be captured first, as described in the following paragraph.)

After finding the native head center, the physician disposes the femur in a natural reference position ("P1"), preferably aligned with femur parallel to the patient's longitudinal axis, while cueing the computer to initialize offset and leg length (step 156) by storing for future reference the tracker position and orientation—in relation to the pelvic plane (as defined by the pelvic tracking marker). Specifically, the position and orientation of the femoral tracking marker 68 is located by optical locating system 26 and the data is interpreted by the computer 32. The position and orientation of the femoral tracking marker 68 essentially defines a position on the femur; this position is related to the pelvic tracking marker and hence the PTMRF by some initial offset, length ("leg length"), and rotation angle which are calculated and stored for future comparison (in navigation steps, described below). Note that the initial vector relationship between the femoral tracking marker and the pelvic marker provides an arbitrary reference for relative comparison. The measurements are not absolute, and are useful only so long as the attachment point and geometry of the femoral tracking marker 68 remains fixed with respect to the femur. Similarly, the attachment point and geometry pelvic tracking marker remains fixed in relation to the pelvis. Nevertheless, the relative position and orientation information suffices to permit meaningful comparison of the pre-operative with the post-operative position.

Permanent fixation of the entire trackable markers is not absolutely required during all phases of the surgery: more accurately, it is required that the relationships between the markers (femoral and pelvic) and their respective bones should be repeatably capable of establishment in a given relationship. For surgical convenience, in some embodiments at least parts of a trackable marker can be detachable from a fixed apparatus used to secure the marker to the bone. The prior relationship between tracker and the bone can be re-established upon re-attachment, by employing a coupling system which insures accurately defined and repeatable coupling relationships between the markers and the bone-fixed apparatus.

It is also quite advantageous during step 156 to calculate a transformation $T_{pf}$ evaluated at the natural position P1. This transformation is used later in the procedure to transform the head center into femoral coordinates, assuming that the femur will be returned to the natural reference position P1. The transformation is then stored, along with the position and orientation information pertaining to the femoral tracking marker (in position P1).

These steps complete the initial acquisition of geometry (step 40 of FIG. 1).

Anatomical Coordinate Systems:

At this point some general explanation of certain anatomical reference systems is relevant and helpful to the understanding of the invention. In the explanation of the invention we refer to various coordinate systems (equivalently, "frames of reference"), often switching systems freely for convenience of explanation or visualization. It should be understood that the choice of a coordinate system is in many cases either arbitrary or a matter of convenience (either for explanation or calculation). Accordingly, different authors have employed differing coordinate systems to describe the geometry of the human hip. Some useful systems are described in Nikou et al., "Description of Anatomic Coordinate Systems and Rationale for Use in an Image-Guided Total Hip Replacement System," in *Medical image Computing and Computer-Assisted Intervention (MICCAI)*, (Pittsburgh, P., Springer, 2000), pp. 1188-1194. In our discussion we shall refer primarily to a pelvic coordinate system and to a femoral coordinate system. Unless otherwise specified, these should be understood to refer respectively to a) a coordinate system imagined to be attached to and moving in concert with the patient's pelvis, and b) a coordinate system imagined to be attached to and moving in concert with the patient's femur (that femur which is the subject of the replacement surgery).

Because the femur can and will be moved in relation to the pelvis, both by pivoting and more freely by dislocating the hip, a time-varying relationship $T_{pf}(t)$ will exist between the pelvic coordinate system and the femoral coordinate system. As described below, by virtue of the locating system 26 and various trackable markers, the computer 32 can dynamically calculate at any instant a mathematical transformation which will express in the pelvic coordinate system any location given in the femoral system, or vice-versa. Similarly, vectors or angles can easily be translated from one system to the other.

It should also be understood that the axes and origin of either the pelvic or femoral reference systems are somewhat arbitrary. For visualization it is convenient to refer to the pelvic system with an origin at a point of symmetry or anatomical landmark. However, for purposes of calculation it is equally valid and often more convenient to define the origin at some point fixed on the fixed pelvic trackable marker. So long as the trackable marker is fixed relative to the pelvis (or if the relationship thereto can be accurately recaptured), the system relative to the marker is perfectly suitable for all calculations. If necessary, the translation to another more well known anatomical system can be easily calculated. Similarly, for the femoral coordinate system a reference frame defined in relation to the femoral trackable marker is suitable for most calculations, and will precisely define any relationship to the femur provided that the femoral marker remains fixed in relation to the femur (or the relationship can be recaptured accurately).

Figure 9:
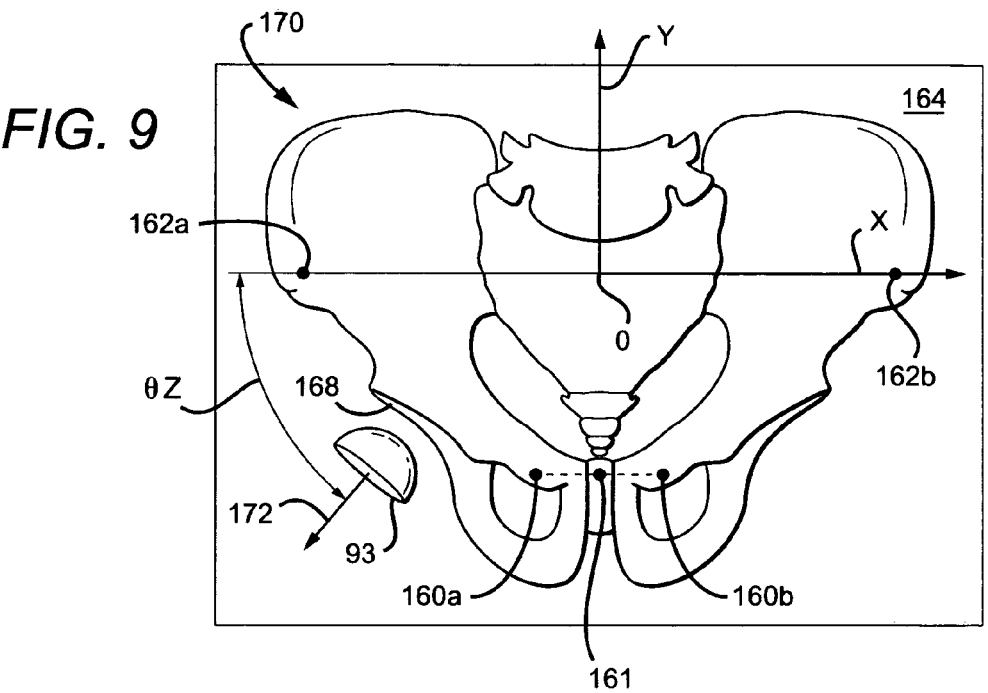
FIG. 9 is a frontal view of a pelvis, defining the pelvic plane, a pelvic coordinate system, and an abduction angle.
Figure 10:
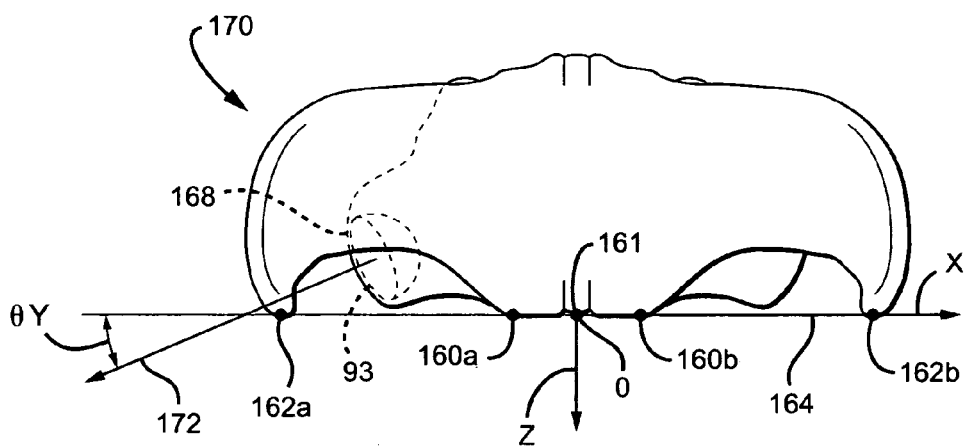
FIG. 10 is a top view of the pelvis of FIG. 9, defining a version angle.

FIGS. 9 and 10 show the pelvis and -define the anterior pelvic plane and pelvic coordinate system which references the angle of the acetabular shell implant. Right and left pubic tubercles 160*a* and 160*b* are shown, as well as the midpoint 161, in relation to right and left anterior superior iliac spines (right 162*a* and left 162*b*). All four typically lie on or near the anterior pelvic plane 164; we define the anterior pelvic plane by the three points: Right and left ASIS 162*a* and 162*b* and the midpoint 161 between the pubic tubercles. We define an origin O on the pelvic plane and located halfway between the right and left ASIS 162*a* and 162*b*. From the origin and pelvic plane we define right-handed, orthogonal Cartesian coordinates as shown, such that the XY plane is the pelvic plane and a Z axis is normal to the pelvic plane intersecting at origin O. An adetabular opening 168 is shown in pelvis 170. We can define the significant angles of the acetabular shell component, relative to our pelvic coordinate system. We define the axis 172 of the shell component as a vector normal to the plane defined by the rim of the component. The vector 172 intersects the plane at the center of the circle of described by the rim. With the axis 172 thus defined, we can define its orientation by $\theta z$ (abduction), $\theta y$ (version) and $\theta x$ (anterior/posterior flexion). $\theta z$ defines rotation about the z axis; it is shown as the angle of the projection of the vector 172 into the XY plane. Similarly, $\theta y$ defines rotation about the Y axis; it is shown as the angle of the projection of 172 into the XZ plane. The abduction angle $\theta z$ is conventionally measured from the negative Y axis; the version angle, from the negative X axis (for a right leg as shown) or the X axis (for a left leg). The third angle ("flexion", not shown) similarly defines rotation about the X axis, and is conventionally measured from the negative y axis. Flexion angle should preferably also be measured and displayed in the method of the invention.

Note that these coordinates are equivalent to the "Anatomical" reference frame defined by Jaramaz et al. in "Computer Assisted Measurement of Cup Placement in Total Hip Replacement," in *Clinical Orthopaedics and Related Research*, No. 354, pp. 71-81 (1998, Lippincott, Williams and Wilkins) (their FIG. 2). We have used the normal vector 172 in place of the cup plane used by Jaramaz, for ease of visualization; but both define the orientation of the cup in an equivalent way. Note that other reference frames such as the "Radiographic definition" and the "Operative definition" are also frequently used in the literature. A definition in the Anatomic reference frame can be converted to either the Radiographic or Operative reference frame by mathematical transformation (preferably performed by computer 32). Please refer to the Jaramaz article, op. cit., for more details on the various frames of reference.

A "femoral coordinate system" is sometimes defined as in Nikou, cited above. For purposes of our explanation it is sufficient to use any femoral frame of reference which is fixed in relation to and moves in concert with the operative femur. It is often convenient to simply calculate femoral coordinates in relation to some point on the femoral tracking marker 68, once said marker has been fixed to the patient's femur.

Nikou further describes a "femoral component coordinate system" which is defined in relation to a femoral implant head. For our purposes such a system is inconvenient. Rather, we will refer to a "Trial stem" coordinate system which is defined in relation to an implant stem.

Figure 11:
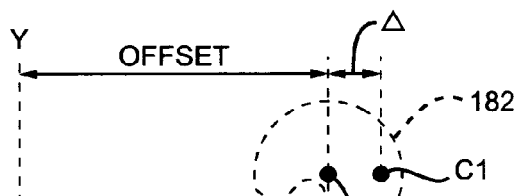
FIG. 11 is a perspective view of a trial implant stem, showing a trial stem coordinate system defined in relation to the implant stem and relationship to a native femoral head center (Cl)
Figure 13:
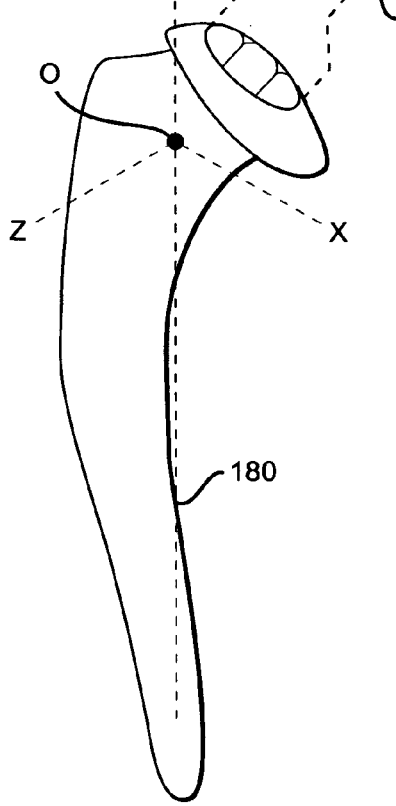
FIG. 13 is a partially exploded perspective view a trial implant stem in relation to a marker which, when fitted onto a trial stem, permits optical tracking of the trial stem.
Figure 13:
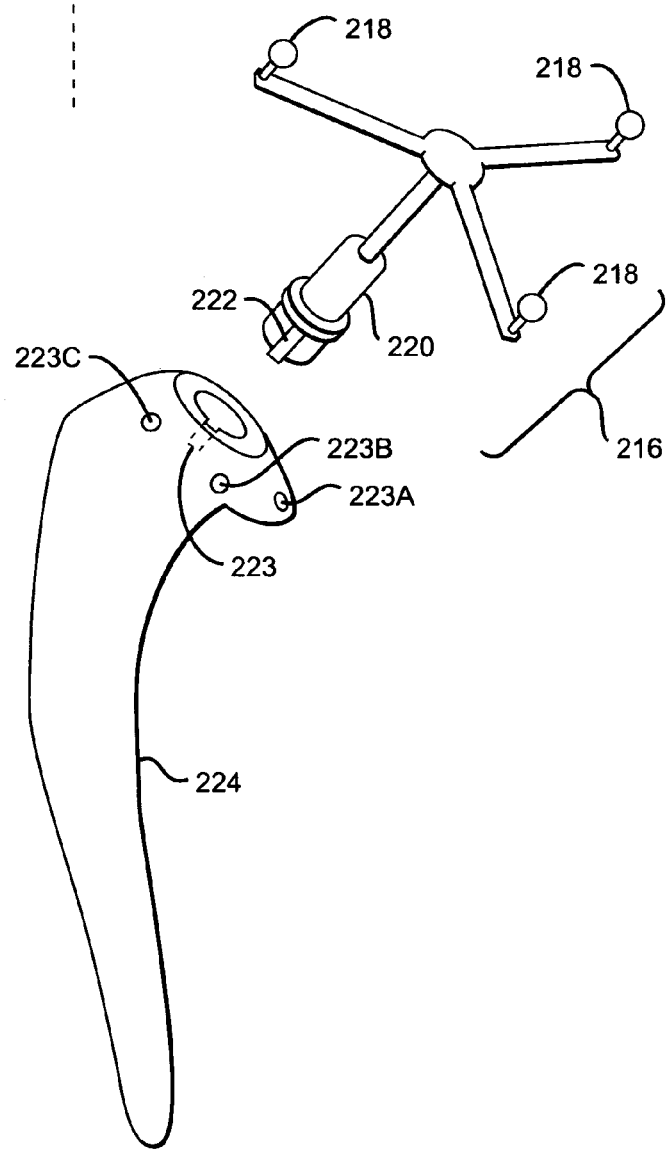

FIG. 11 shows a trial stem 180 with an "implant stem coordinate system" defined in relation to said stem. A Y axis is defined along the long axis of the trial stem 180. An origin O is set by definition at some point O on the Y axis, for example at the top shoulder of the trial stem 180 as shown. One method of definitively locating the origin is by providing an unambiguous indexing feature in the stem, as discussed below in connection with the flow chart of FIGS. 12a-12c. X and Z axes are conveniently defined perpendicular to the Y axes and in fixed relation to the trial stem. Because the trial stem will not in general be rotationally symmetrical about the Y axis, it is important to rigidly define the X and Z axes in relation to some feature of the trial stem (such as a major axis or an ovoid stem, for example).

FIG. 11 also shows in phantom the outline 182 of the femoral head (which will have been removed in preparation for the trial stem). The (phantom) femoral neck 184 is also shown, along with C1 (the "native head center") and C2 (a desired implant head center). C1 and C2 may differ by some (three-dimensional vector) displacement A.

Figures 12B, 12C:
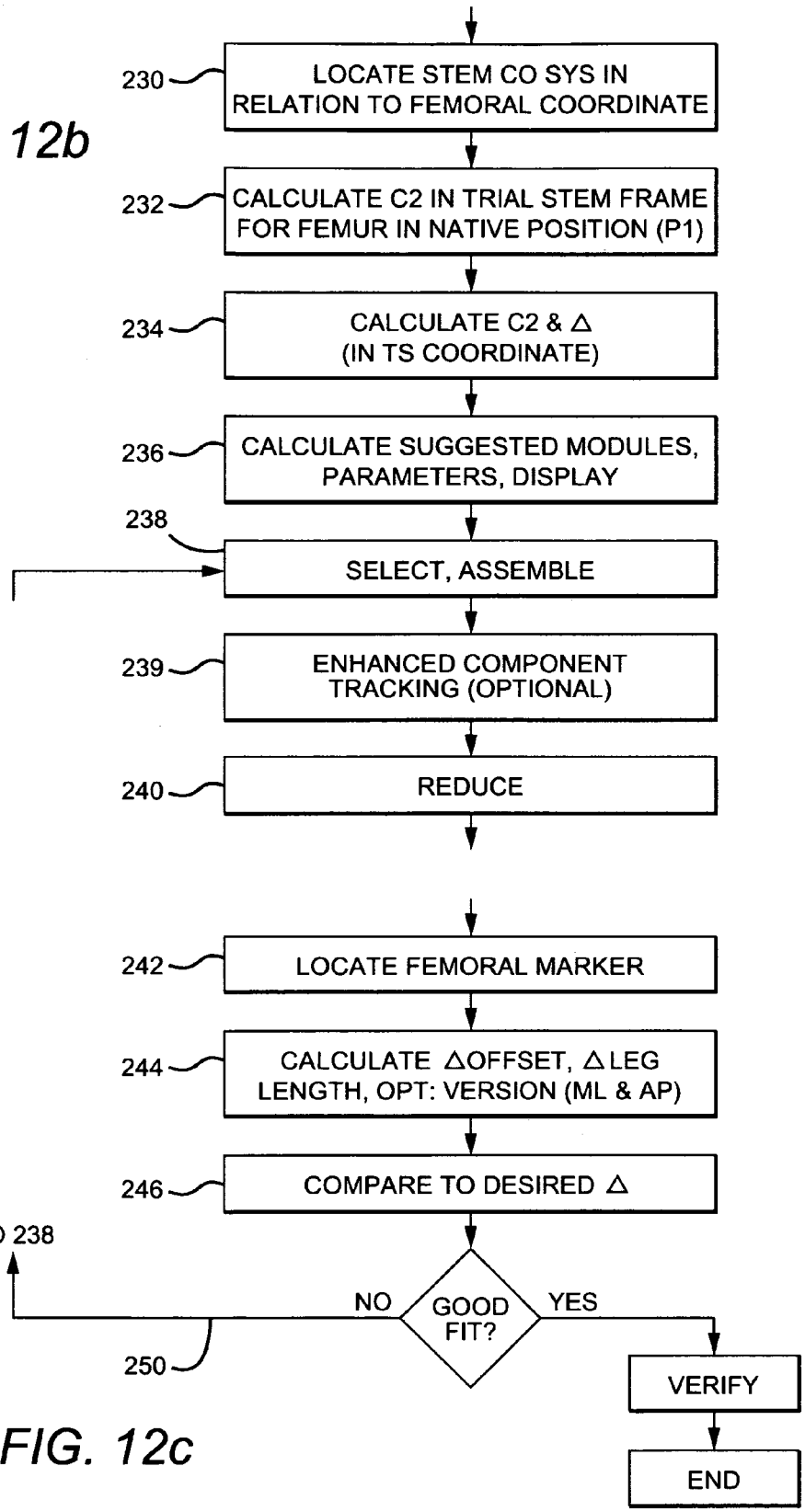
FIG. 12b is a flow diagram continuing from FIG. 12a and showing detailed further steps for executing the navigation step of FIG. 2.
FIG. 12c is a flow diagram continuing from FIG. 12b and showing the detailed remaining steps for executing the navigation step of FIG. 2.

Surgical Navigation:

FIGS. 12a-12c. show detailed steps of the surgical navigation step of the method (step 42 of FIG. 2, above). References to version and abduction can be easily visualized by reference back to FIGS. 9 and 10 above.

With reference to FIG. 12a, first (in conventional surgical step 200) the physician will dislocate the hip and ream the acetabulum to prepare for location of an acetabular implant component ("shell"). These techniques are well known in the surgical arts and are not described here.

Once the acetabulum is prepared for the implant, the physician (in step 202) navigates placement of the acetabular implant shell using the optically trackable insertion tool 94 (described previously in connection with FIG. 7) along with the locating system 26 Specifically, the trackable insertion tool is fixed to the implantable cup. The surgeon then manipulates the insertion tool so that its head is engaged rotatably in the prepared acetabulum. The tool is tracked by the optical locating system 26 and its orientation is displayed via the computer 32 on the display device 34, thus providing feedback as to the abduction angle, and version angles of the implant cup relative to the anterior pelvic plane. The physician manipulates the tool to align with a desired abduction angle and version angle (determined as discussed previously in connection with FIG. 9). When the computer indicates that the desired angles have been attained, the surgeon uses impaction to firmly place the acetabular cup component. A specific angle is not mandated by the invention, but rather the choice of the angle is left to the physician. Fixing screws of various types can also then be used to augment fixation of the shell, as is known in the medical arts.

Navigation step 202 implicitly includes several tracking. and computation actions performed by the computer 32 based on tracking information from the locating system 26. Specifically, the optical tracker 26 allows the computer 32 to calculate a (time varying) orientation of the long axis 95 of the insertion shaft, which is fixed in known relation to the acetabular shell component. The computer 32 then compares this orientation with the (time varying) orientation of the pelvic reference plane, as determined in real time by tracking the fixed pelvic marker (implanted in step 146 above) and thereafter applying the inverse transformation (previously determined from step 150 above). Based upon the calculated time-varying relationship between the pelvic reference frame and the insertion shaft, the computer calculates from time to time the abduction angle and version angle and displays that angle for the surgeon, preferably in relation to some desired "target" angle (previously input by the surgeon). Note that the method does not require the patient to remain immobile between defining the pelvic plane (step 148) and navigation (step 202), because any motion of the pelvis is tracked by the fixed pelvic tracking marker 60 and thereafter compensated by the computer's calculations. Thus, in the computer's geometric model the computer compensates for movement of the pelvic plane, and determines the relationship between the acetabular shell component and the pelvic reference plane in real time.

The specific geometric calculations, performed by the computer in real time, are of no concern to the surgeon in the operation. From the surgeon's viewpoint, to properly align the shell he merely moves the insertion tool tentatively while observing the display (34 in FIG. 1) for feedback. Preferably, the display includes some target or reference pattern (for example, a crossed-hairs target or two protractor displays, one for version and the other for abduction angle). It has been found that 45 degrees of abduction ($\theta z$) and 20 degrees of version ($\theta y$) will typically yield an acceptable result (minimize the number of post-surgical dislocations). A range of 40 degrees +/−10 (abduction) and 15 degrees +/−10 (version) is acceptable, measured in the radiographic definition. The precise angle and range is entrusted to the discretion of the physician, based on his experience and available literature. See DiGioia et al., "Image Guided Navigation System to Measure Intraoperatively Acetabular Implant Alignment," *Clinical Orthopaedics and Related Research*, No. 355, pp 8-22 (1998 Lippincott, Williams and Wilkins); Lewinnek, et al., "Dislocations after Total Hip Replacement Arthroplasties," *Journal of Bone and Joint Surgery*, Vol 60A, No. 2, (March 1978). Once the proper orientation has been established, the shell component is set by impaction and/or screws, according to the implant system.

The orientation of the implant shell 93 is preferably next verified (step 204) by touching at least three distinct, well-spaced and non-collinear points on the rim of the acetabular implant shell 93 with the tip 52 of probe 50 and inputting the three positions via the locating system 26. The three or more points are used by the computer to define the plane of the shell opening, which is normal to a vector 172. The orientation angles of the vector 172 (or equivalently, that of the plane of the shell opening) is then displayed to the physician and preferably recorded for future reference. Preferably, all of angles $\theta x$, $\theta y$ and $\theta z$ are displayed and recorded.

Typically a bearing liner is then fixed to the shell, as is known in the orthopaedic arts. Before fixing the liner, however, the liner position can be adjusted. Today's modular liners typically allow for independent adjustment of the position and orientation of the modular liner within the shell. Preferably, in step 206 the physician can capture the contour of the liner by touching at least three distinct, non-collinear points on the liner rim with the trackable manual probe. In one embodiment, only three points are used. The optical locator and computer capture the contour of the liner and preferably calculate the opening angle and orientation of the liner's rim or lip. Typical liners are not hemispherical, but may have a complex shape including, for example, an extended lip or a complex chamfer. The calculated angles are then displayed to the user. The liner is then typically fixed in the shell. A still further check of proper liner placement can be optionally performed by again touching at least three points on the liner rim (step 206) to verify the position after fixation.

These steps complete the placement of the acetabular shell component (and liner).

Next, the physician uses (step 208) a trackable tool to find the desired implant head center (C2) of the acetabular shell (with liner). Specifically, this can be conveniently located with the aid of the insertion tool 94 described above or a similar tool, as follows. First, the physician replaces the head of the insertion tool with a generally spherical head (102 in FIG. 7) having an outer radius which fits the inner radius of the acetabular shell liner (already implanted). The physician then pivots the insertion or similar tool while maintaining full engagement of the spherical head in the concave liner shell. Optical targets 98 on the insertion tool are tracked by the optical locating system 26. The computer 32 then receives the optical locating data. Substantially simultaneously the computer receives similar tracking data regarding the pelvic reference tracker. The computer then calculates the relationship between the orientation of the insertion tool and the substantially pelvic reference frame (at a specific time), and from that result calculates the center about which the tool has been pivoted (C2). Because of the liner thickness, acetabular shell orientation and position, and acetabular reaming, C2 will not in general coincide with C1. In fact, the physician may intend to displace C2 from the native head center (C1). This choice is left to the judgment and discretion of the physician.

Next, the physician will turn his attention to the femoral component (i.e., stem, neck, and head) of the hip replacement.

The physician will implant (step 210) a trial femoral stem by conventional surgical methods not described here. An illustrative videotape of a narrated surgery is published by Knitted, Inc. in Camarillo, California under the title "Total Hip Arthroplasty." Briefly, the femoral head is removed and the femoral canal is broached in preparation to receive a trial implant stem. The trial stem is then inserted and fixed in the femur. At this point the method of the invention departs again from conventional surgical technique.

In conventional surgical implantation of a modular hip prosthesis, the surgeon would at this stage try various combinations of neck and head components in an attempt to discover the components which will best produce a desired change in leg length and offset. Although calculational aids such as charts are provided by the manufacturer of the prosthesis, these aids can only approximately predict leg length and offset because they do not account for variables such as the depth of insertion of the stem, the angle of insertion, the rotational angle of the stem ("neck version"), and other variables. In conventional surgical methods, another missing datum is the actual implant head center C2 and its relationship to C1.

Because the surgeon in conventional replacement procedure does not have access to real time, intraoperative measurements of the above mentioned variables, the proper choice of modular components is difficult. At best the surgeon can employ a "trial-and-error" procedure to arrive at a combination of components which seems to give a good range of motion, leg length and offset. Such a trial and error procedure, however, may require numerous reductions and dislocations of the hip joint to exchange components, causing trauma to the tissues and consuming surgical time and effort.

In contrast, the method of the invention can eliminate or greatly abbreviate the trial-and-error required to produce the desired leg length and offset.

Returning to the steps of the method as shown in FIG. 12a, according to the invention the physician provides (step 212) as input to the computer the desired change in at least one of leg length and offset. This input can be provided at any stage in the surgery, or even pre-operatively.

Next, the physician cues the optical locating system 26 to acquire the position and orientation of the trial stem and input the position information into the computer 32. In one embodiment of the invention this information is acquired by optically tracking a tool which is at least momentarily placed in a predetermined fixed relation to the trial stem. For example, a trackable tool can be used having a feature which is formed to engage or mate in a predetermined relationship with a complementary feature on the trial stem. One example of such a mating combination tool and trial stem is shown generally at 216 in FIG. 13. The features mate in a deterministic, fixed manner. Optical targets 218 are fixed on a tool neck 220 at a previously known distance and in known geometrical relationship with an indexing feature 222. Feature 222 engages in a predetermined mating relationship with a complementary recess or other receiving feature 223 in trial stem 224. Based on a previously stored geometrical relationship between the targets 218 and the trial stem 224, the tracking data from optical targets 218, and given a previously stored definition of the mating relationship between the tool 216 and the trial stem 224, the computer 32 is able to calculate the exact position and orientation of the trial stem (relative to the femoral trackable marker 68).

After the tool 216 is fixed properly on the trial stem, the surgeon indicates that the relationship is ready for input, for example by clicking a foot pedal in response to a menu prompt. In response, the locating system 26 in step 226 inputs tracking information into the computer, which in turn calculates the position and orientation of the trial stem 224. At substantially the same time the locating system also inputs the location of the femoral trackable marker (68, previously discussed). Based on the locations and orientations of both marker 68 and trial stem 224, the computer calculates the spatial relationship between the trial stem and the femoral coordinate system. More specifically, the position of a landmark on the trial stem is calculated relative to the femoral tracking marker; a set of rotations and translations is also determined which defines the position and direction of the trial stem in relation to the femoral coordinate system. Equivalently stated, the relationships between the femoral coordinate system and a trial stem coordinate system are determined. These relationships are suitably used to calculate a transformation matrix $T_{ft}$ (and inverse, $T_{tf} = T_{ft}^{-1}$) which will convert coordinates in the femoral reference coordinate system into corresponding coordinates in the trial stem coordinate system (and vice-versa).

In another embodiment of the invention, the position and orientation of the trial stem (relative to the femur) are input to the computer by touching a plurality of landmarks on the stem with an optically trackable probe (such as the tool 50 in FIG. 3, or similar). A series of indexing marks or indentations, for example, can be touched by the probe while cueing the computer to input the position and orientation of the probe 50. At least three such indexing marks are greatly preferred in order to establish unambiguously the position and orientation of the trial stem. The position and orientation of the stem is calculated and related to that of the femoral tracking marker. This procedure provides alternative but equivalent steps 226 and 230.

Thus, continuing in FIG. 12*b*, in step 230 it is convenient for the computer to define the trial implant coordinate system, fixed in relationship to the trial stem. The orientations of the trial stem axes are also rigidly defined, being established unambiguously by a rigid feature or asymmetry of the trial stem and the corresponding, complementary feature of the stem locating tool (or landmarks). The computer calculates the transformations which relate the trial stem coordinate system to either or both of the femoral and pelvic coordinate systems, by known mathematical methods.

Next, in one embodiment the computer calculates (step 232) the modified C2 expressed in the trial stem coordinate system. More accurately and specifically, it is convenient for the computer 32 to calculate the coordinates of the desired modified C2 in the trial stem coordinate system assuming that the femur were positioned in position 1 (native leg position P1) as previously recorded. This calculation will provide the direction and displacement of the desired center C2 of the implant head, relative to the trial stem (already fixed in the femur). For this purpose the transformation $T_{pf}$ evaluated at position P1 is used (previously calculated and stored in step 156. If not previously computed, the transformation is now computed based on the stored data defining the position and orientation of the femoral tracking marker in position P1). Note that it is not necessary to actually return the femur to P1: the translation is a "virtual" return.

Specifically, to transform a set of coordinates known in pelvic coordinate system into the trial stem coordinate system, a compound transformation can be used. For example, we wish to find the trial stem coordinates of C2 assuming that the leg will be returned to the natural reference position P1. This is given by:

$$C2\,(X_{ts}) = T_{ft} T_{pf}^{\,0}\,[C2\,(X_p)]$$

Where $C2(X_{ts})$ is C2 in trial stem coordinates, Tpf0 is the transformation from pelvic to femoral coordinates evaluated at position P1; $C2(X_p)$ is C2 expressed in pelvic coordinates, and $T_{ft}$ is the transformation from femoral to trial stem coordinate system.

Typically, but not necessarily, the surgeon will want to change at least one of the leg length or offset by some increment delta. If such a modification is desired, in step 234 the computer will calculate a modified head center position (c2+ Δ, where it is understood that both c2 and Δ are in this context vectors in the trial stem coordinate system).

After the modified C2 is calculated, the computer is prompted to display (step 236) a set of (at least one) suggested options for module combinations or adjustments which will substantially satisfy the requirement that the implant head center be placed at the desired modified head center. Typically a surgeon. will have the option to select from among a number of components having different neck angles, neck lengths. Other parameters may be variable either by selection or adjustment as well, such as the depth of insertion of implant stem into implant head. In some implant systems the angle of anterior/posterior version is also adjustable (for example, by inserting an indexed neck component into one of a plurality of positions indexed in the trial stem). Such options are described, in relation to one suitable modular implant system, in "The Apex Modular Stem", available from Apex Surgical, Lakeville, Mass.

In order to easily compute a combination of modules that will satisfy the desired geometry, the computer should preferably have previously stored a database of parameters describing the measurements and shapes of available implant components, indexed by model numbers, as well as options for adjustment during assembly. These could conveniently be provided by the manufacturer on optical storage medium such as CDROM, for example. Sterile components stored in sealed packaging could optionally be identified with both human readable model numbers and with machine readable codes (for example, with bar code). Optionally, the computer can verify that the appropriate component package has been selected by the surgeon.

At least one, and preferably more than one, of the following variable component parameters should be available (by input or by storage) to the computer: neck anteversion, head offset, neck length, and neck angle of the available components. Other parameters such as variable head seating depth or any other geometric variable should also be considered by the computer to compute suggested module selections or adjustments.

To determine the component combinations, the computer performs the relatively simple operation of calculating, for various component combinations, the direction and distance which the combination will produce between the trial stem shoulder and the head center (of the prosthetic component combination) . This calculation is based on the known and stored geometries and dimensions of the available components. The predicted displacement and direction of the prosthetic head center is then simply compared with the desired modified C2 and either accepted or rejected, based on substantial correspondence within a set of predetermined margins of error.

Obviously, this calculation and comparison is facilitated by use of the trial stem coordinate system. However, the geometric calculations could alternatively be performed purely in the femoral coordinate system, provided that the actual orientation of the trial stem is respected in the calculations. For example, to find the head center of a component combination, a vector addition can be performed in the femoral coordinate system, comprising a summation of: a) a vector from the femoral origin to a known point on the stem axis; plus b) a vector directed along the stem axis to a known point on the neck component; plus c) a vector along the direction of the neck component from the known point to the point of head attachment; plus d) the depth along the neck axis from the point of head attachment to the center of the head component. The directions of each vector must be respected and expressed in the common, femoral component system. Although this alternative method is available and suitable, transformation into trial stem coordinates will often simplify calculation. After calculation, and also as part of step 236, the computer suitably displays suggested modules on output device (34 in FIG. 1). Preferably a number of options will be displayed. The surgeon the makes a choice of components, in step 238. The components are assembled to the trial stem and the hip is reduced (step 240). After reducing the hip, the computer 32 can perform calculations to model a return of the femur position to reference position "P1" (as used in this context, "position" should be understood to include rotational orientation). Alternatively, the physician can physically return the femur to the natural reference position, "P1" established in step 154 above. This position is manually achieved by moving the femur to a position and orientation which approximately matches the orientation of the femur which was previously initialized (in step 156). The locating system 26 once again determines the position of the femoral marker (step 242) and calculates (step 244) at least one of the change in leg length and offset as compared with those initialized in step 156, above. Note that in the present invention the absolute leg length and offset are at no time required. For successful surgical navigation it suffices to track and calculate the difference between the initial femoral tracker position (while the leg is in position 1) and the later tracker position (step 212, while leg is in position 1 again).

Although choice of suitable components, aided by the invention, will generally be sufficient to closely approach a desired post-surgical hip relationship, with certain modular joint systems a further option is available: Some modular systems allow significant adjustment by varying the position in which the components are assembled. For example, certain hip implant systems manufactured by Osteoimplant Technology, Inc. (OTI) and others allow insertion of the neck component into the stem component at selectable positions of rotation about an insertion axis. In other words, neck anteversion is adjustable by rotationally adjusting the position of the neck component during its insertion into the stem component. (Further details are available from OTI in Hunt Valley, Md., and from other manufacturers of hip implants.) Thus, in some embodiments of the invention a further step 239 is preferably employed (after assembly and before reduction). In such embodiments the invention includes calculating with a digital computer a recommended assembly option, based on said calculated relationship between the stem component and the femur. The recommended assembly position is chosen from among a plurality of assembly options to produce the desired post-surgical hip relationship; and a trial or permanent implant is assembled in the recommended position.

According to a further aspect of the invention, ("Enhanced Component Tracking" or ECT of step 239) the manner of assembly of a modular implant system can be further assisted by direct tracking of the modular components during assembly. This procedure will generally be performed in connection with trial components, then permanent components will be substituted before the end of surgery; however, the procedure described could also be performed directly using permanent implant components. In this aspect of the invention, either indexing features or a trackable tool are affixed to a first component of a modular implant system. For example, either the trackable tool 216 (shown in FIG. 13), or else trackable features such as machined indentations, could be provided on a stem component of a hip implant system. Next, a second modular component is provided with (at least one) index feature or a second trackable marker. For example, see the hip neck component in FIG. 17, discussed below.

In accordance with the ECT aspect of the invention, the locating system and computer are used to track the relationship between a first component and a second component of a modular implant system during assembly and adjustment. The locating system and computer first track, from time to time, the position of the first component (in the manner previously described in connection with the femoral stem implant). The first and second component are then assembled in a trial position. Typically, the physician will manually input into the computer one or more identification codes which identifies the specific components to the computer. The computer and locating system then acquire the position of the second component (by capturing the position of one or more index feature(s) on the second component), while substantially simultaneously recording the position of the tracked first component. Manifestly, this operation requires the use of two or more trackable markers, but only one locating system is required.

After acquiring the locations of the index features on the second component, the computer consults a database of previously input and stored information characterizing the specific components that are currently tracked. Among the parameters stored should be the dimensions of the components and the position of the index features on such components (relative to extent and geometry of the specific component). Next, based upon both the tracking data and the previously stored information base, the computer calculates the relationship between the first and second component (both positional offset and relative orientation). In some embodiments, the position and relative orientation of a particular, significant feature of the second component may be directly calculated: for example, if index features are placed on a hip neck component in a predetermined relationship to the axis of the neck, then the axis can be directly calculated from the acquired position of those index features. Thus, it is possible to directly measure the geometric relationship between a tracked stem and a neck axis affixed to said stem. The effect of various neck angles can then be tracked.

Similarly, the method can be used to track a hip head component in relation to a neck component, by tracking index features on the head component.

The amount and kind of tracking information which can be acquired will depend, in a particular embodiment; on the number and kind of index features, and on the use of a database of previously determined module relationships and dimensions. For example, two index features will generally suffice to uniquely track a hip head module in relation to the neck module. Three neck features are convenient to determine the position and angle of a neck module. Fewer features may be sufficient if the stem axis is tracked, and the insertion angle of the neck component into the stem component is previously known and recorded.

In a variation of this method, it is possible to indirectly relate second, third, and further components each to a primary component (such as a stem implant) by inference, without continuously tracking the primary implant component. This is accomplished as follows: First, a first bone (such as the femur) is tracked by a first trackable marker. Next, a (trial or permanent) primary implant component (stem) is implanted. The position and orientation of the primary implant component is then acquired, as previously described, by using a trackable tool or index features on the primary component. The computer then calculates the (vector) relationships between the primary component and the first bone (femur). Once this relationship is calculated, it is possible to calculate the position and orientation of the primary component indirectly, by continuing to track the femur (and assuming that the femoral tracker and stem remain fixed in relation to the femur). Next, the locating system and computer are used to acquire the position of the secondary component by tracking index features on the secondary component. The position of the secondary component is then compared with the simultaneous, inferred position of the primary component. The (vector) relationship between the secondary component is the calculated (for example, by rotating coordinates and subtracting vectors).

The indirect variation of the ECT method. is advantageous in that it does not require the continuous presence of a tracker on the primary component (stem) Once the position of the stem is acquired, it can be tracked from time to time by indirectly by inference from the femoral tracking marker. The relationship between secondary components and the primary component can then be calculated during trial assemblies: various neck and head combinations can be attempted and the resulting hip geometries can be calculated easily.

In general, step 244 will determine some departure from the desired head center, offset and/or leg length. This change may be insignificant, but if in the judgment of the surgeon it is significant (and undesirable) he may either (1) change one or more of the prosthetic components to better approach a desired geometry, or (2) drive the implant stem deeper into the femur. The steps 244 and 246 and/or 212 would then be repeated until a desirable geometry is obtained. In many cases, the desired geometry may be a significant change from the pre-operative leg length and offset. The choice is within the discretion and control of the surgeon. This completes the "navigation" step (step 42 of FIG. 2).

In many cases a surgeon will prefer to check the range of motion of the trial implant by pivoting the reduced joint while checking for impingement between neck and liner. If significant impingement or joint laxity compromises range of motion, the surgeon can repeat portions of the trial procedure by inputting a modified desire for change in offset (for example, increasing the offset produces a tighter joint, where ligaments have been tensioned) then looping back by path 250 to step 238. The trial steps can be repeated until the desired restoration is obtained. The tracking and computation provided by the method should reduce the number of trials below that which would have been required in a conventional, "trial and error" procedure; but it in no way prevents the surgeon from exercising independent judgment of the joint's integrity. The method of the invention allows the surgeon's first trial assembly to better approach his desired post-operative geometry, even before any trial reduction is attempted. Each further trial thereafter is also facilitated by use of the computer to better predict the components shape and measurements which will best approach a desired fit.

Aspects of the above described method can be described as intra-operatively digitally modeling a "virtual reduction" of a hip to predict a fit of a proposed implant system without unnecessarily traumatizing the ligaments and other tissues. Such a virtual reduction results in time savings and decreases cost and risk to a patient. The virtual reduction is accurate in that it is preferably modeled on the actual, optically tracked position of the trial stem (located by the optical locating system and an optical trackable marker). This method is far superior to mere consultation of a chart or table to choose modular components. Conventional charts or tables are based only on rough estimates of the trial stem position and of the patient's skeletal measurements, which are often inaccurate.

This completes the surgical navigation of step 42 in FIG. 2

Changes in Offset and Leg-Length:

FIG. 14 shows aspects of geometry involved in the method of determining the change in leg length, offset, and optionally anteversion. Point 330 represents the position vector of an arbitrary point on the femoral tracker as tracked and acquired during acquisition step 154. (For clarity, the femoral trackable marker is not shown.) Point 332 represents the position vector of the corresponding point of the femoral tracker, as sampled after the implantation in step 242. Small vector 334 represents the vector subtraction of the vector 332 from the vector 330. The vector subtraction is readily calculated, and it can be decomposed into components (projections) in any desired plane, by conventional vector geometry. The projection into the pelvic plane is convenient, but that into the central coronal plane could also be used.

Optionally, a parameter known as "anterior/posterior offset" can also be measured and predicted with the method of the invention. This parameter measures the degree of translation of the hip toward the front or back of the patient's body. Ideally, the post-surgical relationship between the femur and the pelvis should match, in all three degrees of freedom, a desired post-surgical position. In practice, it will often be sufficient to attain a good match in only one or more of the parameters leg length, offset, and anterior-posterior offset. Accordingly, the goal of the invention is to aid in attaining a post-surgical outcome matching at least one of the three listed parameters.

Figure 15:
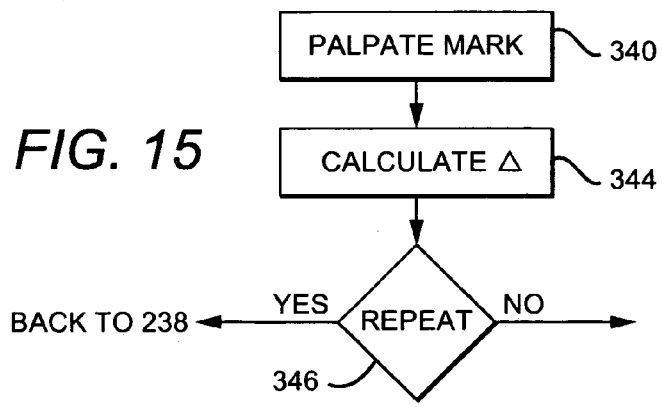
FIG. 15 is a flow diagram showing detailed steps suitable for executing the verification step of FIG. 2.

Verification:

FIG. 15 shows details of the optional but highly preferred verification step (44 in FIG. 2). First, in synchrony with program execution, the physician uses the probe tip (52 FIG. 3) to touch the reference mark (cauterization or equivalent) which he previously made in step 148. The optical locator and computer calculate (step 344) the relationship between the reference mark and the fixed pelvic tracking marker (60 in FIG. 4) or femur tracker. For example, the computer might calculate the position of the reference mark in the pelvic marker's reference frame (PTMRF). This position is compared with the previously calculated position of the marker in the same reference frame (from step 148) and the result is output for the physician's information. Based on the result, he/she may then either choose (step 346) to revise the procedure (via return path 348, because the check shows that something moved) or end the surgery (if the check shows insignificant movement). This procedure provides a redundant "tracker check" feature which reassures the physician that the tracking accuracy has not been compromised due to unintentional tracking marker movement.

Preferably, a similar tracker check procedure should be performed to check the fixation of the femoral tracking marker: during initialization the physician may make a reference mark on the femur, then after the implantation he can touch the mark and check for slippage by finding the coordinates of the reference mark in the reference frame of the femoral tracking marker 68.

Finally, it is highly desirable that the system records a permanent record of the procedure, or at least a summary suitable for inclusion into the patient's file. FIG. 16 shows a typical screen capture or printout which includes acetabular shell version and abduction (as measured by the insertion tool), shell angles, liner angles, head center change, leg length change, and leg offset change. It is also convenient to provide a machine readable record of the surgery, on a medium such as CD-R or its equivalent.

Optically Aided Component Identification:

Another aspect of the invention, "Optically Aided Component Identification," exploits the available optical locating system (26 in FIG. 1) and optically trackable markers which facilitate identification or characterization of specific implant components. Specifically, in one embodiment the invention uses the manual trackable probe (50 in FIG. 3, discussed above) in conjunction with a system of predefined identifying features asociated with one or more of the implant components. The method of optically aided component identification will be described in relation to a modular hip prosthesis comprising a stem component, a neck component, and a head component. Although such a system is used in a typical embodiment of the invention, the invention is not limited to use with hip prostheses, but could also be used with other implant systems, including but not limited to knee replacements, ankle replacements, shoulder replacements and other implants.

Figure 17:
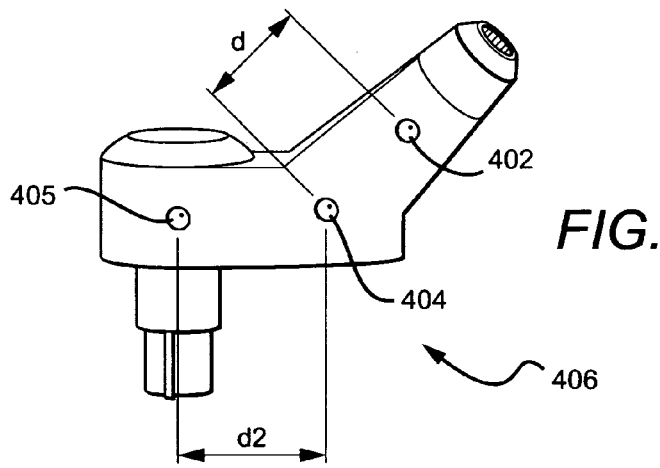
FIG. 17 is a perspective view of an implant stem component with features for use in a method of optically aided component identification.

Referring now to FIG. 17, the method of optically aided component identification employs two or more pre-defined index features such as indentations 402 and 404 formed in, fixed to, or otherwise permanently associated with an implant component (406). For example, FIG. 17 shows suitable features formed in a neck component of a modular hip implant system. (Although a neck component is shown, the features and the method of identification could be used in relation to other implants or components, including but not limited to hip, knee, or other orthopedic implants). The figure shows two small shallow recesses 402 and 404, suitably conical in form, similar to the familiar conical recess often used to countersink screws. The two features 402 and 404 are spaced a predetermined distance (d) apart, wherein the distance d is controlled according to a pre-defined system. A system is defined wherein each degree of distance d is associated with and signifies a characteristic, parameter, or model of the component on which the features are formed. For example, a manufacturer can establish a predefined database (system of associations) whereby each degree of distance d is uniquely associated with one or more of: a component type, component model number, a component size or dimension, or a component geometry. In other words, the distance d which separates features 402 and 404 on each component acts as a product identification signifier. Thus, by measuring the distance d on a specific component (preferably optically, as described below) a computer (32 in FIG. 1) is enabled to identify and/or characterize the component by reference to a database. Alternately, in a simple variation, the component could be characterized or identified by reference to a formula rather than a database: for example, in a simple system the distance d can be in direct relation to a component dimension (such as neck length). In a very simple system the relationship can even be a linear ratio.

FIG. 17 also shows a further feature 405 which is displaced a distance d2 from feature 404. This illustrates that more than two features could optionally be provided. In an embodiment with more than two index features, more information can be conveyed by the plurality of relationships between features. For example, in FIG. 17 three non-collinear features are shown, defining a triangle. The lengths of the (3) sides of the triangle (404-405-402), as well as the three angles of the triangle, could all be used to convey encoded identification or characterization information (by reference to a pre-defined system of correspondences). For example, the angle at vertex 405 could designate a model number, while the displacement between 404 and 402 might denote a neck size or angle. The correspondences need not be directly in proportion to the physical characteristics of the component; an arbitrary system of correspondences could be employed. On the other hand, a simple system of proportionality could be used for representing dimensions or geometry of the component.

Optionally, one or more of the indexing features pertinent to the method of optically aided identification could optionally be one (or more) of the same features used in-a navigational step, such as the alternative to steps 226 and 230 (discussed above in connection with FIG. 12*a*).

It should also be noted that the index features could be provided either in one or both of a) a temporary component (such as a "trial" stem of a hip implant system) or b) a final, permanent implant component.

Figure 18:
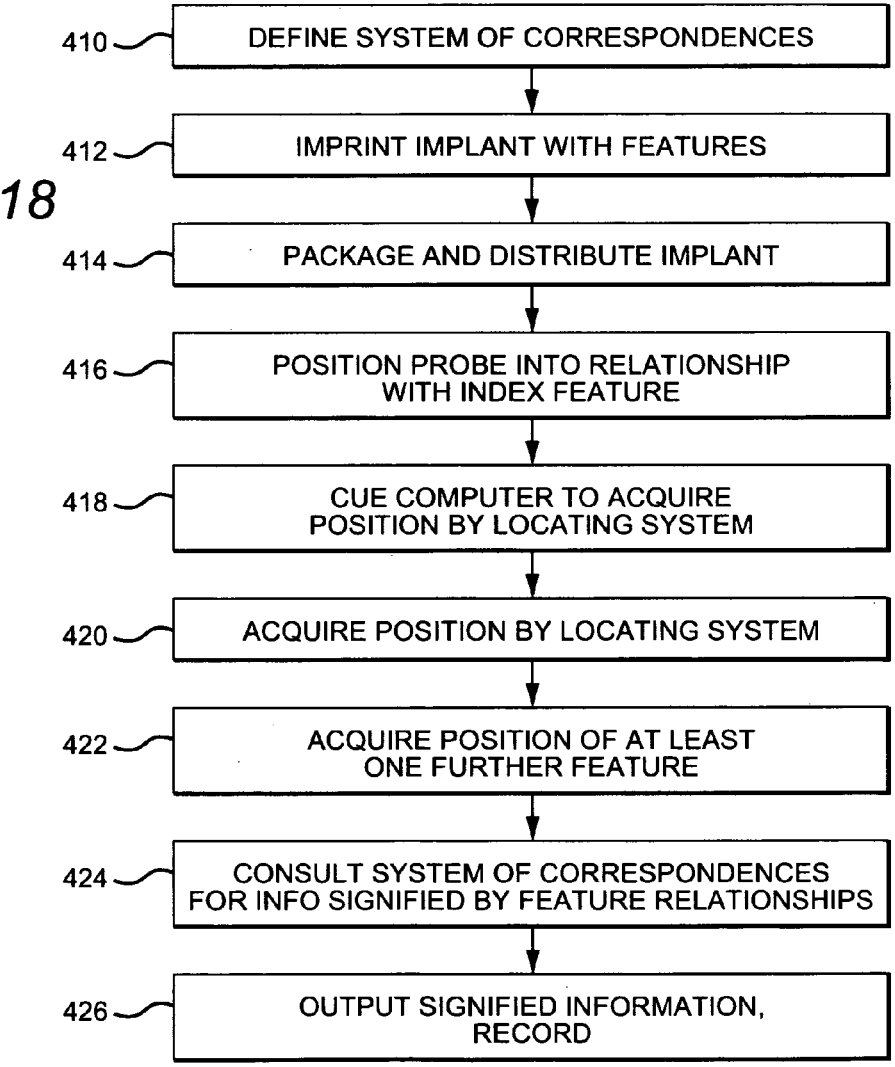
FIG. 18 is a flow diagram showing steps in a method of optically aided component identification.

Steps of an optically aided method of identifying a component are shown in FIG. 18. The method is suitable for use with either trial or permanent implantable components. Preliminary steps 410-414 are preferably performed well in advance of any surgical procedure, and would typically be performed by a manufacturer or supplier of the implant system before distribution of the implant components. First, a system of correspondences and signifiers is defined (step 410). For example, a database, table, or formula is established which relates geometry and/or dimensions of identifying features with certain dimensions, model numbers, or other parameters of implant components. The correspondences will usually be one to one, but one to many or many to one could be used in some applications. Next, (in step 412) a specific individual component or implantable device is "imprinted" with two or more features (such as 402 and 404 of FIG. 16). The features are applied to the component in a specific predetermined relationship chosen by consulting the predetermined system of correspondences for the signifier which correctly identifies the specific component to be imprinted. Next, the components are typically packaged and distributed for use (step 414) and the defined system of correspondences is also distributed (typically as a computer readable database or table).

Later, during or closely before a surgical procedure, the remaining steps 416-424 are performed to identify, characterize, or verify a pre-marked surgical component. Pursuant to or incidental to a surgical procedure, the surgeon will access an optical locating system (26 in FIG. 1), a computer (32 in FIG. 1) and a manual trackable probe (50 in FIG. 3). At some point in a surgical procedure, during or incidental to computer aided navigation as described above in connection with FIGS. 1-16, a surgeon may desire to identify, verify or characterize an implant or implantable component. The surgeon cues the computer by manual input that a component identification is to be performed (step 416) he then manipulates the manual probe into a defined relationship with an index feature (such as 402) on the specific implant to be identified. Suitably, the defined relationship will be a positive mating or engagement, as with a conical probe tip with a female, conical recess such as that shown for 404. Accordingly, the manual probe tip should suitably have a shape which is complementary to and adapted to engage with the index features in the components to be identified. Other types of positive engagement can be used, provided that the type of contact, mating, or engagement provides a repeatable, identifiable relationship between a known point on the trackable probe and the feature. A marking could be used in a "point and click" procedure; but some method which provides tactile feedback is to be preferred. For example, a conical point on the manual probe can be felt to enter and self-center in a conical depression 404; this tactile feedback aids the surgeon and prevents errors.

Once the feature is in the proper relationship with the probe 50, the surgeon cues the computer 32 (for example, by foot switch, in step 418). The computer then acquires position information (step 420). In most applications at least two trackable markers will be tracked and their relative positions related: first the trackable manual probe 50, and then a second trackable marker which is in fixed relation with the component to be identified. The second marker prevents errors in tracking due to motion of the component during measurement. The computer can eliminate motion of the component as a variable by tracking the motion of a marker fixed to the component. Measurements of the features can then be directly related in the reference frame of the component, regardless of any translation of the component between measurements.

In one embodiment, for example, during a hip replacement surgery (as described above in relation to FIGS. 1-16) a femoral trackable marker (68 in FIG. 5) is fixed to the patient's femur during at least part of the surgical procedure. This femoral trackable marker 68 acts as the second marker for purposes of the method of optically aided component identification. Assume that a stem component of a hip replacement prosthesis bears two or more index features (such as 402 and 404). After implantation of the stem component, as previously described, the marker 68 will be at least temporarily fixed in relation to the stem component (because both stem and marker are fixed to the femur). In this configuration, the femoral trackable marker 68 is continuously tracked by the locating system 26 and computer 32. In the method of optically aided component identification, each index feature (such as 402 and 404) will be located by the locating system 26 in relation to the substantially simultaneous location of the femoral trackable marker 26. By calculating the location of each index feature in the reference frame of the femoral trackable marker 26, the computer is able to unambiguously determine the spatial relationship between the features 402 and 404 notwithstanding any inadvertent movement of the femur (and stem) during the identification procedure.

Note that this method could be varied or extended to other components: for example, a neck component once fitted to a stem is at least temporarily fixed in relation to the femoral trackable marker 68; index features on the neck component can thus be located in relation to the femoral trackable marker 68 by the same method applied to a stem component. Similarly, acetabular implant components can be identified by index features by optically locating the features in relation to the pelvic reference marker (60 in FIG. 4). Alternatively, a trackable marker can be temporarily fixed to the component which is to be identified, which will provide a reference frame to locate the features. As a further alternative, the component in question could be temporarily fixed in relation to the locating system (for example, by a fixture on the operating table or other substantially immovable object).

Referring again to FIG. 18, after acquiring the position of the first feature 402, the computer and tracking system are used to acquire position (step 422) of at least one further feature (404). The distance between the features 402 and 404 is then easily calculated by the computer, if necessary compensating for any (tracked) motion of the component between acquiring the positions of the first and second features. More than two features can be used: if more than two features are used, any or all combinations of distance and geometrical relationships between the features can be used as indices to signified parameters in the predefined database.

After acquiring all requisite feature positions, the computer consults the previously established system of correspondences (database or formula) (step 424) and outputs (step 426) to the surgeon the signified information regarding the specific implant or component which bears the features. For example, size, model number, materials, or other information regarding the implant or component could be displayed and optionally recorded for future reference, along with patient and pertinent medical information regarding the procedure.

The computer assisted identification of implant components is advantageous in that it helps prevent errors during surgery. The use of optical trackers is particularly advantageous in a procedure which otherwise employs optically tracked navigation techniques, because the optically aided method of the invention employs the same trackers used for the computer aided navigation steps of the surgery. Identification of the components by machined or permanently affixed features is advantageous because they can be positively located even in the presence of blood or other effacing substances. Furthermore, features permanently associated with the implant cannot be inadvertently switched (as can markings on packaging). With prior methods, mislabeling is relatively common and is a common cause of medical product recalls. In contrast, the method of optically aided identification of implant components according to the invention offers a more reliable method of verification or identification of component parameters in real time, using tools which will often be already available in the operating room.

It will be easily recognized that numerous and varied features could be used, and that the features used for identification are not limited to recesses. The could include raised features, grooves, bores, ridges, dimples, or any other feature which can be reliably located by a complementary manual probe or tool. They will typically be applied by machining, but could alternatively be affixed by other methods, including plasma etching, e-machining, or less exotic methods such as screws. Various systems of correspondence can be employed to relate the relationships between the features (as indices) to a signified parameter, part number, dimension, or characteristic. By using more than two features, various combinations of geometrical relationships and displacements among the features can be used to signify multiple parameters or characteristics of the implant or component. All such variations are within the scope of the invention.

Although the modular navigation procedures and systems have been described primarily in the context of hip replacement surgery, as previously noted the methods and apparatus of the invention are not limited to hip replacement. By way of example, the apparatus and methods of the invention are particularly advantageous for use in shoulder replacement surgery. In such a procedure a surgeon seeks to accurately place the glenoid component within the scapula, (which requires accurate establishment of inclination and version) to improve range of motion as well as to prevent loosening, excessive wear, and impingement. This aspect of shoulder replacement is analogous to the navigation of the acetabular shell component in hip replacement. Another goal in shoulder replacement is to establish the proper relationship between the humerus and the scapula (angle and distance). This aspect of the operation is analogous to the femoral navigation in the hip replacement surgery. Accordingly, the methods and apparatus described above in connection with the femur and pelvis can be applied to establish a desired post-operative relationship between a humerus and a scapula in a shoulder replacement procedure. In either context, the invention provides a surgical method for fitting a customizable, modular orthopedic implant system for replacing a joint between a first bone and a second bone.

In the context of a shoulder replacement, the first bone would be a humerus; the second bone would then be the scapula. In the context of the hip, the first bone could be the femur, and the second bone the acetabulum. Similarly, in a shoulder replacement a first implant component would be specifically a humeral stem implant component; the analogous component in a hip replacement surgery would be a femoral stem component. While several illustrative embodiments of the invention have been shown and described, numerous variations and alternate embodiments will occur to those skilled in the art. In some operations the acetabular implant might not be required., but the femoral navigation methods and apparatus of the invention are still applicable. The procedure may be repeated on both sides of the body in a bi-lateral THR operation. Different elastomeric straps, fibers, cords, mesh, wire, adhesives or ligatures could be employed in connection with the femoral tracking marker device. The fixed pelvic marker could also be fixed by alternate methods such as clamps, pins or even adhesives. The method can be adapted to various body geometries and sizes, and indeed could even be adapted, with small modifications, for veterinary medicine. Tracking means other than but equivalent to optical could be substituted, such as radio, microwave, magnetic, sonic or ultrasonic tracking systems, provided that the system be not so clumsy or bulky as to interfere with the surgical manipulations required. The geometries of the various tools and markers can be varied or modified to accommodate different tracking approaches. Active or passive, wired or wireless optical targets can be used on the tracking markers. Differing means of calculating geometric relationships, vectors, transformations, and coordinate systems could be employed. Such variations and alternate embodiments are contemplated, and can be made without departing from the spirit and scope of the invention as defined in the appended claims.

We claim:

1. A computer assisted surgical method of fitting a customizable modular hip implant system in a hip arthroplasty procedure, comprising the steps of:
    intraoperatively mounting an optically trackable marker to a femur;
    intraoperatively measuring the position of a native femoral head center (C1) in relation to said optically trackable marker, by tracking the position and orientation of said optically trackable marker via an optical locating system interfaced with a digital computer, while moving the hip joint through a motion consistent with a natural arc of movement;
    placing a stem component of the modular hip implant system in the femur;
    with said optical locating system interfaced with said digital computer, optically and substantially simultaneously tracking both said optically trackable marker and said stem component placed in the femur, to intraoperatively measure the relative position and orientation of said stem component in relation to said optically trackable marker;
    calculating the position and orientation of said stem component in relation to said optically trackable marker, based on the substantially simultaneously measured relative positions and orientations of said stem component and said optically trackable marker;
    determining a desired position for a prosthetic femoral head center (C2);
    transforming the desired position for said desired prosthetic femoral head center (C2) into a stem coordinate system defined in relation to said stem component; and
    selecting, with the aid of a digital computer at least one combination of implant modules which will combine with said stem component to fix a prosthetic femoral head center at the desired position (C2).

2. The method of claim 1, further comprising the step of locating a center of a prosthetic acetabular cup component by tracking a tool;
    said tool having a partially spherical head which rotatably engages said acetabular cup component.

3. The method of claim 1, wherein said step of optically and substantially simultaneously tracking both said optically trackable marker and said stem component comprises: tracking said stem with a trackable tool, said tool having a mating feature adapted to mate in predictable spatial relationship with a complementary feature of said stem.

4. The method of claim 1, further comprising the step of:
    tracking said stem by locating at least one landmark feature on said stem with a trackable tool.

5. The method of claim 1, where said modular hip implant system includes a plurality of interchangeable neck components having differing dimensions.

6. The method of claim 1, where said modular hip implant system includes a plurality of interchangeable neck components having differing neck angles.

7. The method of claim 1, wherein said modular hip implant system includes a plurality of interchangeable femoral head components.

8. The method of claim 1, wherein said desired position of said prosthetic femoral head center is adjusted for an predetermined change in medial-lateral offset of the femur.

9. The method of claim 1, wherein said desired position of said prosthetic femoral head center is adjusted for a predetermined change in leg length.

10. The method of claim 1, wherein said desired position of said prosthetic femoral head center is adjusted for a predetermined change in anterior- posterior offset.

11. The method of claim 1, wherein said desired position of said prosthetic femoral head center is adjusted for a predetermined degree of stem anteversion.

12. The method of claim 1, comprising the further step of:
    calculating with a digital computer a recommended assembly option, based on said calculated relationship between said stem component and said femur, said recommended assembly option chosen from among a plurality of assembly options to produce said desired position of said prosthetic femoral head center.

13. The method of claim 1, wherein said step of intraoperatively measuring the position of a native femoral head center (C1) is performed by using a least-squares surface fitting algorithm to find the center of a spherical surface, assuming that a point on the femur is constrained to lie on a partial spherical surface with its center at the native head center.

14. The method of claim 1, wherein said step of intraoperatively mounting an optically trackable marker is performed by clamping said optically trackable marker to the femur with a removable clamp.

15. A method of customizing geometry of a modular or adjustable hip implant system intra-operatively, comprising the steps of:
- intraoperatively measuring a native relationship between a femur and a pelvis, using trackable markers and a locating system interfaced to a digital computer;
- implanting a stem component of the modular hip implant system in the femur; optically tracking said stem component with an optical locating system;
- digitally modeling post-assembly hip joint geometry with a digital computer based upon known shapes and measurements of available implant components and said intraoperatively measured native relationship between said femur and said pelvis.

16. The method of claim 15, comprising the further step of:
- locating the position and orientation of said stem component using a trackable tool placed in known relationship to at least one index feature of said stem component.

17. The method of claim 16, comprising the further steps of selecting implant modules and/or adjustments based upon said digital model, a desired post-operative hip geometry, and a set of available modular implant components having a plurality of selectable measurements.

18. A computer assisted surgical method of fitting a customizable, modular orthopedic implant system for replacing a joint between a first and second bone, comprising the steps of:
- intraoperatively measuring a native relationship between the first bone and the second bone, with said first and second bones joined by a natural joint, using trackable markers and a locating system interfaced to a digital computer;
- placing a first component of the modular orthopedic implant system in the first bone;
- calculating a desired post surgical relationship between said first bone and said second bone;
- mounting an optically trackable tool on said first component;
- tracking position and orientation of said first component with an optical locating system to intraoperatively obtain a first set of position and orientation information regarding said first component;
- tracking said first bone, to intraoperatively obtain a second set of position and orientation information regarding said first bone; and
- calculating a relationship between said first component and said first bone based on said first and second sets of position and orientation information; and
- predicting, with the aid of a digital computer and based upon the calculated relationship between said first component and said first bone, at least one combination of implant modules which will combine with said implanted first component to produce said desired post surgical relationship between said first bone and said second bone.

19. The method of claim 18, wherein said implant modules are components of a modular hip implant.

20. The method of claim 18, wherein said implant modules are components of a modular shoulder implant.

21. The method of claim 18, wherein said step of predicting includes predicting a combination to produce a desired displacement between said first and second bones.

22. The method of claim 21, wherein said step of predicting includes predicting a combination to produce a desired direction of displacement between said first and second bones.

23. The method of claim 21, wherein said step of predicting further includes predicting a combination to produce a desired angular relationship between said first and second bones.

24. The method of claim 23, wherein said first and second bones are a pelvis and a femur, and wherein said desired angular relationship is a hip neck angle.

25. The method of claim 23, wherein said first and second bones are a pelvis and a femur, and wherein said desired angular relationship comprises a desired rotational angle of a component to produce a desired degree of stem anteversion.

26. The method of claim 18, wherein said step of predicting includes calculating with a digital computer a recommended assembly option, based on said calculated relationship between said stem component and said femur, said recommended assembly option chosen from among a plurality of assembly options to produce said desired post-surgical relationship.

27. The method of claim 18, further comprising the step of:
- intraoperatively tracking with a locating system a relationship between a first component and a second component of a modular implant system, to further aid in assembling said components in a manner to produce a desired post surgical relationship between said first and second bones.

28. The method of claim 27, wherein said step of intraoperatively tracking the relationship between said first component and said second component comprises tracking with a locating system at least one index feature placed on at least one of said components.

29. The method of claim 27, wherein said step of intraoperatively tracking the relationship between said first and said second components comprises indirectly tracking at least one of said components by tracking a bone which is rigidly connected to said at least one of said components.

* * * * *